US009757447B2

United States Patent
Mattsson et al.

(10) Patent No.: US 9,757,447 B2
(45) Date of Patent: Sep. 12, 2017

(54) RECOMBINANTLY PRODUCED ALLERGENS

(71) Applicant: PHADIA AB, Uppsala (SE)

(72) Inventors: Lars Mattsson, Uppsala (SE); Jonas Lidholm, Knivsta (SE); Thomas Lundgren, Uppsala (SE)

(73) Assignee: PHADIA AB, Uppsala (SE)

( * ) Notice: Subject to any disclaimer, the term of this patent is extended or adjusted under 35 U.S.C. 154(b) by 0 days.

(21) Appl. No.: 14/984,482

(22) Filed: Dec. 30, 2015

(65) Prior Publication Data

US 2016/0114031 A1 Apr. 28, 2016

Related U.S. Application Data

(62) Division of application No. 13/375,836, filed as application No. PCT/SE2010/050623 on Jun. 4, 2010, now Pat. No. 9,243,045.

(30) Foreign Application Priority Data

Jun. 5, 2009 (SE) ...................... 0950416

(51) Int. Cl.
*A61K 39/35* (2006.01)
*A61K 39/00* (2006.01)
*C07K 14/47* (2006.01)
*G01N 33/68* (2006.01)

(52) U.S. Cl.
CPC ............ *A61K 39/35* (2013.01); *A61K 39/001* (2013.01); *C07K 14/47* (2013.01); *G01N 33/6854* (2013.01); *G01N 2800/24* (2013.01)

(58) Field of Classification Search
None
See application file for complete search history.

(56) References Cited

U.S. PATENT DOCUMENTS 4,459,360 A 7/1984 Marinkovich

FOREIGN PATENT DOCUMENTS

EP 2000531 A1 12/2008

OTHER PUBLICATIONS

Mattson et al. 'Molecular and immunological characterization of Can f 4: a dog dander allergen cross-reactive with a 23 kDa odorant-binding protein in cow dander.'Clin. Exp. Allerg. 40:1276-1287, 2010.*
K. Kongsuwan et al, Activation of Several Key Components of the Epidermal Differentiation Pathway in Cattle Following Infestation with the Cattle Tick, Rhipicephalus (*Boophilus*) microplus, International Journal for Parasitology 40 (2010), 499-507.
A. Heutelbeck et al, Exposure to Allergens of Different Cattle Breeds and Their Relevance in Occupational Allergy, International Archives of Occupational and Environmental Health (2009) 82: 1123-1131.
NCBI Reference Sequence XP 581277.2, Bos taurus, Jun. 3, 2010.
S. Saarelainen et al, Animal-Derived Lipocalin Allergens Exhibit Immunoglobulin E Cross-Reactivity, Clinical and Experimental Allergy, (2007) 38, 374-381.
J. Rautiainen et al, Molecular Analysis of Allergenic Proteins in Bovine Dander, Allergy 1996: 51:378-382.
S. Saarelainen et al, Assessment of Recombinant Dog Allergens Can f 1 and Can f 2 for the Diagnosis of Dog Allergy, Clinical and Experimental Allergy 2004; 34: 1576-1582.
J. Ylönen et al, Comparison of the Antigenic and Allergenic Properties of Three Types of Bovine Epithelial Material, International Archives of Allergy and Immunology, 1992; 99:112-117.
L. Mattsson et al, Molecular and Immunological Characterization of Can f 4: a dog dander allergen cross-reactive with a 23 kDa odorant-binding protein in cow dander, Clinical and Experimental Allergy, (2010) 1-12.
T. Lundgren et al, Cloning and Characterisation of the dog allergen Can f 4; Journal Compilation, 28th Congress of European Academy of Allergy and Clinical Immunology, Warzawa, Poland, (2009), Allergy 64 (Suppl 90):251, Abstract No. 620.
M. Chapman et al, Recombinant allergens for diagnosis and therapy of allergic disease, Journal of Allergy and clinical Immunology, Sep. 2000, 409-418.
A. Konieczny et al, The Major Dog Allergens, Can f 1 and Can f 2, are salivary lipocalin proteins: cloning and Immunological characterization of the recombinant forms; Immunology 1997, 92 577-586.
L. Mattsson et al, Prostatic Kallikrein: A new major dog allergen, Journal of Allergy and Clinical Immunology, (2009), vol. 123, No. 2, 362-368e3.
A. Custovic et al, Domestic Allergens in Public Places II: dog (Can f 1) and cockroach (Bla g 2) allergens in dust and mite, cat, dog and cockroach allergens in the air in public buildings, Clinical and Experimental Allergy, 1996, vol. 26, pp. 1246-1252.
S. Spitzauer, Allergy to Mammalian Proteins: At the Borderline between Foreign and Self?, International Archives of Allergy and Immunology, 1999; 120: 259-269.

(Continued)

*Primary Examiner* — Nora Rooney
(74) *Attorney, Agent, or Firm* — Porter Wright Morris & Arthur LLP

(57) ABSTRACT

Methods for producing an allergen composition, methods for in vitro diagnosis of type I allergy, and diagnostic kits for performing diagnosis employ Bos d 23k allergen of SEQ ID NO: 4, or the mature protein thereof, or a variant or fragment of the Bos d 23k allergen or the mature protein sharing epitopes for antibodies with the Bos d 23k allergen or the mature protein. Methods for treatment of a Type I allergy to a mammal and pharmaceutical compositions employ a Bos d 23k allergen of SEQ ID NO: 4, or the mature protein thereof, or a variant or fragment of the Bos d 23k allergen or the mature protein sharing epitopes for antibodies with the Bos d 23k allergen or the mature protein, wherein the Bos d 23k allergen, the mature protein, the variant or the fragment is modified to abrogate or attenuate its IgE binding response.

17 Claims, 10 Drawing Sheets

(56) References Cited

OTHER PUBLICATIONS

S. Spitzauer et al, Characterisation of Dog Allergens by Means of Immunoblotting, International Archives of Allergy and Immunology, 1993; 100:60-67.
L. Yman et al, Serum Albumin—An Important Allergen in Dog Epithelia Extracts, International Archives of Allergy and Immunology 44: (1973) 358-368.
H. De Groot et al, Affinity Purification of a major and a minor allergen from dog extract: Serologic Activity of Affinity-Purified Can f 1 and of Can f 1-depleted extract, Journal of Allergy and Clinical Immunology, (Jun. 1991), vol. 87, No. 6, 1056-1065.
Y. Boutin, Allergenicity and Cross-Reactivity of cat and dog allergenic extracts, Clinical Allergy, 1988, vol. 18, 287-293.
R. Movérare et al, Purification and Characterization of the Major Oak Pollen Allergen Que a 1 for Component-Resolved Diagnostics Using ImmunoCAP, International Archives of Allergy and Immunology, 2008; 146: 203-211.
A. Shevchenko et al, Mass Spectrometic Sequencing of Proteins from Silver-Stained Polyacrylamide Gels, Analytical Chemisty, vol. 68, No. 5, Mar. 1996, 850-858.
S. Spinelli et al, The Structure of the Monomeric Porcine Odorant Binding Protein Sheds Light on the Domain Swapping Mechanism, Biochemisty 1998, 37, 7913-7918.
M. Frohman, Rapid Amplification of Complementary DNA Ends for Generation of Full-Length Complementary DNAs: Thermal Race, Methods in Enzymology, vol. 218, 1993, 340-356.
M. Tegoni et al, Mammalian Odorant Binding Proteins, Biochimica et Biophysica Acta 1482 (2000), 229-240.
R. Mäntyjärvi et al, Complementary DNA cloning of the predominant allergen of bovine dander: A new member in the lipocalin family, Journal of Allergy and Clinical Immunology, Jun. 1996, 1297-1303.
K. Lindblad-Toh et al, Genome Sequence, Comparative Analysis and Haplotype Structure of the Domestic Dog, Nature, vol. 438, 2005, 803-819.
Work et al, Laboratory Techniques in Biochemistry and Molecular Biology, Sequencing of Proteins and Peptides, Elsevier Science Publishers B.V., 1981, 184-185.
J. Rouvinen et al, Probing the Molecular Basis of Allergy, The Journal of Biological Chemistry, vol. 274, No. 4, 1999, 2337-2343.
T. Virtanen et al, Immune reactivity of cow-asthmatic dairy farmers to the major allergen of cow (BDA20) and to other cow-derived proteins. The use of purified BDA20 increases the performance of diagnostic tests in respiratory cow allergy, Clinical and Experimental Allergy, 1996, vol. 26, 188-196.
J. Ylönen et al, IgE and IgE antibody responses to cow dander and urine in farmers with cow-induced asthma, Clinical and Experimental Allergy, 1992, vol. 22, 83-90.
R. Valenta et al, The Recombinant Allergen-Based Concept of Component-Resolved Diagnostics and Immunotherapy (CRD and CRIT), Clinical and Experimental Allergy, 1999, vol. 29, 896-904.
B. Åkerstrom et al, Lipocalins: Unity in Diversity, Biochimica et Biophysica Acta 1482 (2000) 1-8.
D. Flower et al, The lipocalin protein family: structural and sequence overview, Biochimica et Biophysica Acta 1482 (2000) 9-24.
G. Gutiérrez et al, Evolution of the lipocalin family as inferred from a protein sequence phylogeny, Biochimica et Biophysica Acta 1482 (2000) 35-45.
R. Mäntyjärvi et al, Lipocalins as allergens, Biochimica et Biophysica Acta 1482 (2000) 308-317.
A. Dewitt et al, Molecular and immunological characterization of a novel timothy grass (*Phleum pratense*) pollen allergen, Phl p. 11, Clinical and Experimental Allergy, 2002, 32:1329-1340.
Dewitt et al, Cloning, Expression and Immunological Characterization of full-length timothy grass pollen allergen Phl p. 4, a berberine bridge enzyme-like protein and homology to celery allergen Api g5, Clinical and Experimental Allergy 36, 2006, p. 77-86.
Blumenthal et al, Definition of an allergen, Allergens and Allergen Immunotherapy. Ed. R. Lockey et al, New York, Marcel Decker, 2004, pp. 37-50.
Ngo et al, Computational Complexity, Protein Structure Prediction and the Levinthal Paradox. The Protein Folding Problem and Tertiary Structure Prediction. Ed. K Merz et al. Boston, Birkhauser, 1994, pp. 491-495.
Skolnick et al, From genes to protein structure and function: novel applications of computational approaches in the genomic era, Trends in Biotech, 18:34-39 (2000).
Mondal et al, Identification of the allergenic proteins of Ipomoea fistulosa pollen: Partial characterization and sensitivity test, Grana, 36:301-305 (1997).

\* cited by examiner

Fig. 3

```
Peptide 1: IAENGPFR
Peptide 2: GEYNGGNYFR
Peptide 3: GAHVNEEDIAK
Peptide 4: GIPEENIIYLGDTDN
```

Fig. 4

| | | |
|---|---|---|
| M  K  I  L  L  C  L  A  L  V  L  A  S  D | 15 |
| ATGAAGATCCTACTGTTGTGTCTTGCACTCGTTTTGGCTTCTGAT | 45 |
| ↓ | | |
| A  Q  L  P  L  P  N  V  L  T  Q  V  S  G  P | 30 |
| GCCCAGCTACCCCTTCCTAATGTACTGACACAGGTTTCAGGACCA | 90 |
| W  K  T  L  Y  I  S  S  N  N  L  D  K  I  G | 45 |
| TGGAAGACGTTGTACATATCATCCAACAACCTTGACAAGATTGGC | 135 |
| D  N  G  P  F  R  I  Y  M  R  G  I  N  V  D | 60 |
| GACAATGGACCGTTTAGGATTTATATGAGAGGTATCAATGTGGAC | 180 |
| I  P  R  L  K  M  S  F  N  F  Y  V  K  V  D | 75 |
| ATACCAAGACTCAAAATGTCATTCAATTTTTACGTCAAGGTTGAC | 225 |
| G  E  C  V  E  N  S  V  G  A  S  I  G  R  D | 90 |
| GGAGAGTGCGTTGAAAACTCTGTTGGGGCATCAATAGGACGAGAC | 270 |
| N  L  I  K  G  E  Y  N  G  G  N  Y  F  R  I | 105 |
| AATCTTATCAAGGGTGAATATAATGGTGGCAATTATTTCCGAATT | 315 |
| I  D  M  T  P  N  A  L  I  G  Y  D  V  N  V | 120 |
| ATTGATATGACCCCAAATGCCCTCATAGGCTATGATGTCAATGTG | 360 |
| D  S  K  G  K  I  T  K  V  A  L  L  M  G  R | 135 |
| GATAGCAAAGGGAAAATCACAAAAGTGGCTTTATTGATGGGCAGA | 405 |
| G  A  H  V  N  E  E  D  I  A  K  F  K  K  L | 150 |
| GGAGCTCATGTTAATGAGGAGGACATTGCAAAGTTCAAGAAGCTG | 450 |
| S  R  E  K  G  I  P  E  E  N  I  I  Y  L  G | 165 |
| AGTAGAGAAAAGGGTATTCCAGAAGAAAATATTATATACTTAGGC | 495 |
| D  T  D  N  C  P  N  H  E  * | 174 |
| GATACTGACAACTGTCCCAACCATGAATAA | 525 |

Fig. 10

```
Can f 4    QLPLPNVLTQVSGPWKTLYISSMNLDKIGDNGPERIYMRGINVDIPRLKMSFNFYVKVDG 60
           .|..|||::||.:||..:||.:||.:.       .|||||.|
Bos d23k   ..EAQGDASQFTGRWLTYYTAANNIEKITEGAPFHAFMRYLEFDENGTILMHFYVKENG5  8

Can f 4    ECVENSVGASIGRDNLIKGEYNGGNYFRIIDMTPNALIGYDVNVDSKGKITKVALLMGRG12 0
           :|.:|.|||||||.:.:.|||  .|:|.:.||||  |||:.   |:|
Bos d23k   ECIE.KYASGTKEENFYAVDYAGHNEFQLIRGDANSLLTHNVNVDEDGKETELVQLFGKG 117

Can f 4    AHVNEEDIAKFKKLSREKGIPEENIIYLGDTDNCPNHE 158
           |||||||||:  ||||||||||||||
Bos d23k   NNVEPEYKEEYYNTVREKGIPEENILNFIDNDNCPEE.  154
```

RECOMBINANTLY PRODUCED ALLERGENS

RELATED APPLICATION

This application is a divisional application of U.S. Ser. No. 13/375,836 filed Dec. 2, 2011, which is a 371 of PCT/SE2010/050623 filed Jun. 4, 2010.

SEQUENCE LISTING

The present application incorporates by reference the Sequence Listing filed herewith entitled "188762A-Sequence-Listing.txt", created Dec. 30, 2015 and having a size of 6606 bytes.

FIELD OF THE INVENTION

The present invention relates to the field of allergy. More specifically, the invention relates to the identification of novel allergens from mammals and to diagnosis and treatment of allergy towards mammals.

BACKGROUND

Dog dander is a common cause of indoor allergy with symptoms including rhinitis, conjunctivitis, bronchial inflammation and asthma. Dog allergens can be detected not only in houses where dogs are kept as pets but also in other places such as schools and day care centres where dogs are not present on a regular basis [1].

Allergy to dog is accompanied and dependent of sensitization to proteins released from dog hairs and dander. In cases of suspected allergy to dog, the clinical investigation includes assessment of sensitization by skin prick or specific IgE antibody measurement using extract of dog hair and/or dander. A laboratory immunoassay for specific IgE, such as a Phadia ImmunoCAP®, can detect most cases of sensitization to dog using natural dog dander extract due to favourable assay conditions and a large solid phase available for allergen attachment.

Dog hair and dander extracts contain a complexity of allergenic and non-allergenic proteins [2, 3]. Four dog allergens have so far been identified and studied in detail: Can f 1, Can f 2, Can f 3 and Can f 5 [4-6]. The former two are both members of the lipocalin protein family and have been purified and expressed as recombinant proteins [4, 7]. Can f 3, dog serum albumin, is a relatively conserved protein showing extensive cross-reactivity to other mammalian albumins [8]. Can f 5, dog prostatic kallikrein, has recently been described as a major dog allergen and shown to cross react with human prostate-specific antigen (PSA) [5]. Of the dog dander allergens known to date, Can f 1 and Can f 5 appear to be most important, binding IgE antibodies from approximately 50% and 70% of dog allergic subjects, respectively [5, 9]. Although about 20-40% of adult dog allergic individuals display IgE antibody binding to Can f 2 or Can f 3, few appear to react exclusively or even dominantly to either of these allergens [5, 9]. In a recently reported study, it was found that a small proportion of dog allergic patients display IgE antibody binding to none of Can f 1, Can f 2, Can f 3 and Can f 5, despite being sensitized to natural dog dander extract [5].

In addition to the allergens discussed above, an IgE-reactive, 18 kDa lipocalin-like protein, distinct from Can f 1 and Can f 2, has been reported and designated Can f 4 [9]. Fifteen of 25 (60%) dog allergic patients were reported to display serum IgE reactivity to this 18 kDa band in immunoblotting, making this a potentially important dog allergen component. However, the allergen has only been characterised as a 13 amino acid N-terminal sequence from an SDS PAGE gel, a sequence yielding no match to any known protein sequence from dog. The full protein sequence is thus unknown, and cloning of a recombinant protein has not been performed. Neither has the native protein been purified, and no suggestion is given as to how cloning of Can f 4 could be accomplished.

In an abstract by Saarelainen et al. published in the Abstract Book of the 3rd International Symposium on Molecular Allergology in Salzburg Apr. 18-20, 2008, it is stated that Can f 4-specific mAb recognized a protein of 20 kDa in cow dander extract.

In a special edition of the scientific journal Allergy publishing the abstracts of the XXVIII Congress of the European Academy of Allergy and Clinical Immunology (EAACI) in Warsaw Jun. 6-10, 2009, there is an abstract disclosing that a cDNA encoding a full-length Can f 4 has been cloned [Allergy 64 (Suppl. 90): 179-538). However no indication is given as to how this cloning could be achieved and no nucleic acid or amino acid sequence is given.

SUMMARY OF THE INVENTION

The inventors have identified a need in the art for further characterisation and validation of the significance of the allergen Can f 4.

As stated above, a laboratory immunoassay for specific IgE can detect most cases of sensitization to dog using natural dog dander extract due to favourable assay conditions and a large solid phase available for allergen attachment. However, in a miniaturized or non-laboratory immunoassay, such as an allergen microarray or a doctor's office test, the combination of less favourable assay conditions, lower capacity for antibody-binding allergen reagent and natural allergen extract of limited potency, has been found to cause insufficient diagnostic sensitivity. A similar situation may exist also for immunoassays for specific IgE to other animal epithelia. Thus, there is a need in some cases to use pure allergenic proteins to achieve sufficient sensitivity in diagnostic tests for specific IgE. Another need for the use of recombinant allergen components is given by the concept of component-resolved diagnostics [24]. According to this concept the analysis of the IgE response to individual allergen components rather than to whole allergen extracts enables a better distinction between cross reactive allergen sensitisations and original allergen sensitisations. Thus there is a need to identify and produce as a recombinant protein all potential allergen components from a particular allergen source.

The present inventors experienced problems when trying to sequence and clone Can f 4 by use of standard methods known in the art. The problems were only solved by using unconventional methods, as described below in the Results section. The present invention is based on the unexpected finding of IgE antibody binding to both dog and cow dander extract, and the understanding that in order to identify the nucleic acid sequence and to accomplish the cloning of Can f 4, the inventors had to correlate Can f 4 to a protein from another organism.

In one aspect the invention relates to a recombinantly produced Can f 4 allergen.

In another aspect the invention relates to a nucleic acid coding for said recombinantly produced Can f 4 allergen.

In further aspects the invention is related to a vector comprising said nucleic acid, and a host cell comprising said vector.

In still another aspect the invention relates to a recombinantly produced Can f 4 allergen for use in an in vitro diagnosis of Type I allergy.

Another aspect of the invention relates to a method for producing an allergen composition, comprising the step of adding a recombinantly produced Can f 4 allergen to a composition comprising an allergen extract and/or at least one purified allergen component.

In a further aspect the invention relates to an allergen composition "spiked" with recombinantly produced Can f 4 allergen. Such an allergen composition may be an allergen extract or a mixture of purified and/or recombinant allergen components having no or a low Can f 4 allergen content, wherein the recombinantly produced Can f 4 allergen is added in order to bind IgE from patients whose IgE would not bind or bind poorly to the other allergen components in the composition. This aspect of the invention also relates to a method for producing such a composition, which method comprises the step of adding a recombinantly produced Can f 4 allergen to an allergen composition, such as an allergen extract (optionally spiked with other components) or a mixture of purified native or recombinant allergen components.

In yet a further aspect the invention relates to an in vitro diagnostic method for diagnosing a Type I allergy in a patient, wherein a body fluid sample such as a blood or serum sample from the patient is brought into contact with a recombinantly produced Can f 4 allergen or a composition according to the previous aspect, and it is detected whether or not the patient sample contain IgE antibodies that bind specifically to recombinantly produced Can f 4 allergen, wherein the presence of such IgE antibodies specifically binding to said Can f 4 allergen, is indicative of a type I allergy. Such a diagnostic method may be carried out in any manner known in the art. The recombinantly produced Can f 4 allergen may e.g. be immobilized on a solid support, such as in a conventional laboratory immunoassay, in a microarray or in a lateral flow assay.

In a further aspect the invention relates to a diagnostic kit for performing the method according to the previous aspect, which kit includes a recombinantly produced Can f 4 allergen.

The invention further relates to a method of treatment of Type I allergy to a mammal, comprising administering to an individual in need of such treatment a recombinantly produced Can f 4 allergen, or a form thereof that is modified to abrogate or attenuate its IgE binding response, as explained below. In one embodiment the mammal is a dog. In another embodiment the mammal may be any one having a mammalian allergen showing homology to a recombinantly produced Can f 4 allergen, provided that the individual show IgE cross-reactivity with said mammalian allergen, such as Bos d 23k. This aspect of the invention also relates to the use of a recombinantly produced Can f 4 in such immunotherapy, including e.g. component-resolved immunotherapy. Examples of modifications include, but are not limited to, fragmentation, truncation or tandemerization of the molecule, deletion of internal segment(s), substitution of amino acid residue(s), domain rearrangement, or disruption of at least in part of the tertiary structure by disruption of disulfide bridges or it's binding to another macromolecular structure, or by removal of the protein's ability to bind low molecular weight compounds.

In another aspect the invention relates to a recombinantly produced Can f 4 allergen, or a form thereof that is modified to abrogate or attenuate its IgE binding response, as explained below, for use in the treatment of Type I allergy.

In yet another aspect the invention is related to a pharmaceutical composition comprising a recombinantly produced Can f 4 allergen, or a form of said Can f 4 allergen that is modified to abrogate or attenuate its IgE binding response.

In the above mentioned aspects, the recombinantly produced Can f 4 allergen may be replaced by a variant or fragment thereof sharing epitopes for antibodies with wildtype Can f 4 allergen, as defined below.

In one embodiment of every above mentioned aspect, the recombinantly produced Can f 4 allergen has an amino acid sequence according to SEQ ID NO: 2, and is encoded by a nucleic acid sequence according to SEQ ID NO: 1.

Furthermore the invention relates to a recombinantly produced Can f 4 allergen having an amino acid sequence according to SEQ ID NO: 2 for use in diagnosis as well as for use in therapy.

The invention further relates to a recombinantly produced Bos d 23k allergen for use in an in vitro diagnosis of Type I allergy.

Another aspect Of the invention relates to a method for producing an allergen composition, comprising the step of adding a recombinantly produced Bos d 23k allergen to a composition comprising an allergen extract and/or at least one purified allergen component.

In a further aspect the invention relates to an allergen composition "spiked" with recombinantly produced Bos d 23k allergen. Such an allergen composition may be an allergen extract or a mixture of purified and/or recombinant allergen components having no or a low Bos d 23k allergen content, wherein the recombinantly produced Bos d 23k allergen is added in order to bind IgE from patients whose IgE would not bind or bind poorly to the other allergen components in the composition. This aspect of the invention also relates to a method for producing such a composition, which method comprises the step of adding a recombinantly produced Bos d 23k allergen to an allergen composition, such as an allergen extract (optionally spiked with other components) or a mixture of purified native or recombinant allergen components.

In yet a further aspect the invention relates to an in vitro diagnostic method for diagnosing a Type I allergy in a patient, wherein a body fluid sample such as a blood or serum sample from the patient is brought into contact with a recombinantly produced Bos d 23k allergen or a composition according to the previous aspect, and it is detected whether or not the patient sample contain IgE antibodies that bind specifically to recombinantly produced Bos d 23k allergen, wherein the presence of such IgE antibodies specifically binding to said Bos d 23k allergen, is indicative of a type I allergy. Such a diagnostic method may be carried out in any manner known in the art. The recombinantly produced Bos d 23k allergen may e.g. be immobilized on a solid support, such as in a conventional laboratory immunoassay, in a microarray or in a lateral flow assay.

In a further aspect the invention relates to a diagnostic kit for performing the method according to the previous aspect, which kit includes a recombinantly produced Bos d 23k allergen.

The invention further relates to a method of treatment of Type I allergy to a mammal, comprising administering to an individual in need of such treatment a recombinantly produced Bos d 23k allergen, or a form thereof that is modified to abrogate or attenuate its IgE binding response, as explained below. In one embodiment the mammal is bovine. In another embodiment the mammal may be any one having a mammalian allergen showing homology to a recombinantly produced Bos d 23k allergen, provided that the individual shows IgE cross-reactivity with said mammalian allergen, such as Can f 4. This aspect of the invention also relates to the use of a recombinantly produced Bos d 23k in such immunotherapy, including e.g. component-resolved immunotherapy. Examples of modifications include, but are not limited to, fragmentation, truncation or tandemerization of the molecule, deletion of internal segment(s), substitution of amino acid residue(s), domain rearrangement, or disruption at least in part of the tertiary structure by disruption of disulfide bridges or it's binding to another macromolecular structure, or by removal of the protein's ability to bind low molecular weight compounds.

In another aspect the invention relates to a recombinantly produced Bos d 23k allergen, or a form thereof that is modified to abrogate or attenuate its IgE binding response, as explained below, for use in the treatment of Type I allergy.

In yet another aspect the invention is related to a pharmaceutical composition comprising a recombinantly produced Bos d 23k allergen, or a form of said Bos d 23k allergen that is modified to abrogate or attenuate its IgE binding response.

In the above mentioned aspects, the recombinantly produced Bos d 23k allergen may be replaced by a variant or fragment thereof sharing epitopes for antibodies with wild-type Bos d 23k allergen, as defined below.

In one embodiment of every above mentioned aspect regarding Bos d 23k, the recombinantly produced Bos d 23k allergen has an amino acid sequence according to SEQ ID NO: 4, and is encoded by a nucleic acid sequence according to SEQ ID NO: 3.

Definitions

Can f 4 should be construed as the dog allergen listed by the International Union of Immunological Societies Allergen Nomenclature Sub-Committee (www.allergen.org).

Lipocalins should be construed as the large and diverse group of proteins, present in a wide range of organisms and involved a multitude of functions [25-27]. They are characterized by certain conserved structural features but are otherwise not highly conserved in amino acid sequence. Lipocalins are capable of binding small, mainly hydrophobic molecules, including steroids, fatty acids and pheromones. One subgroup of lipocalins present in the mammalian olfactory apparatus are referred to as odorant binding proteins due to their ability of reversibly binding and releasing of volatile compounds involved in olfactory signalling [28]. Several mammalian lipocalins have been reported as allergens, causing respiratory allergy symptoms in sensitized humans [29].

The protein named Bos d 23k by the inventors is described in the Example as a 23 kDa protein purified from cow dander, comprising an amino acid sequence in agreement with a hypothetical bovine gene product, described in Acc. No. XP_581277, deduced from a *Bos taurus* genomic sequence.

The term "Can f 4", not further specified, should be construed as a full-length, unmodified, intact Can f 4.

The same definition also applies *mutatis mutandis* to Bos d 23k.

Variants and fragments of a Can f 4 allergen sharing epitopes for antibodies with Can f 4 allergen should be construed as being those fragments and variants whose binding of IgE antibodies from a serum sample from a representative Can f 4 allergen sensitized patient can be significantly inhibited by Can f 4 allergen. Such an inhibition assay may e.g. be performed according to the protocol disclosed in Example 8 of WO 2008/079095. The variants and fragments are also said to have similar IgE-binding properties to the Can f 4 allergen.

The same definition also applies *mutatis mutandis* to Bos d 23k.

A form of said Can f 4 allergen that is modified to abrogate or attenuate its IgE binding response should in the context of the present invention be construed as meaning a Can f 4 allergen that has been chemically or genetically modified to change its immunological properties, e.g. as exemplified above in relation to the immunotherapy aspect of the invention.

The same definition also applies *mutatis mutandis* to Bos d 23k.

Homologue allergen should be construed as meaning an allergen in which the nucleic acid sequence is able to hybridize to the nucleic acid sequence of another allergen. The outcome of the hybridization may depend on the length of the sequences, on how the homology is distributed over the sequences, and on the experimental conditions, such as salt concentration, temperature, wash stringency, etc. A homologue allergen according to the present invention may have an overall sequence identity lower than what is often regarded for a homologue, i.e. 65-70%. By the definition of this invention the nucleic acid sequence of a homologue allergen may show a lower overall sequence identity to the nucleic acid of another allergen, but still hybridize to this other allergen due to segments of the sequences showing higher sequence identity.

Cross-reactivity to an allergen should be construed as meaning that an individual's IgE antibodies to a first allergen are also reactive to a second allergen that may or may not be a homologue to the first allergen.

BRIEF DESCRIPTION OF DRAWINGS

FIG. 2A, Preparative size exclusion chromatography. Pooled fractions are indicated by vertical bars. FIG. 2B, Anion exchange chromatography. Hatched line indicates conductivity (right y-axis). Fractions pooled for further purification are marked by a horizontal bracket. FIG. 2C, Reversed phase chromatography. Hatched line indicates acetonitrile concentration (right y-axis). Fractions pooled for further purification are marked by a horizontal bracket. FIG. 2D, Anion exchange chromatography. Hatched line indicates conductivity (right y-axis). The peak containing the pure target protein is indicated by an arrow.

FIG. 3 shows the peptide sequences obtained from tryptic fragments of the purified 16 kDa dog dander protein, showing Peptide 1 (SEQ ID NO: 9), Peptide 2 (SEQ ID NO: 10), Peptide 3 (SEQ ID NO: 11), and Peptide 4 (SEQ ID NO: 12).

FIG. 4 shows the cDNA sequence (as depicted by SEQ ID NO: 1 in the appended sequence listing) and deduced amino acid sequence (SEQ ID NO: 2) of Can f 4. The predicted signal cleavage site is marked by an arrow.

FIG. 5A, Analytical gel filtration. Hatched line: nCan f 4

(right y-axis); solid line: rCan f 4 (left y-axis). Elution volumes of 6.5, 13.7, 29, 43 and 75 kDa calibrator proteins are marked by diamond symbols. FIG. 5B, SDS-PAGE of non-reduced (ox) and reduced (red) samples of nCan f 4 and rCan f 4. The sizes of relevant MW marker proteins are indicated to the left. FIG. 5C, Analysis of IgE antibody binding activity ($kU_A/L$) by ImmunoCAP. Sera from 37 dog allergic subjects were analysed. Hatched lines indicate the 0.10 and 0.35 $kU_A/L$ levels.

FIG. 8A, Fractionation by size exclusion chromatography. The top fractions from two of the peaks marked A and B were pooled and subjected to reducing SDS PAGE analysis (insert). The sizes of relevant MW marker proteins are indicated to the right.

FIG. 8B, SDS-PAGE of reduced (red) and non-reduced (ox) samples of purified Bos d 23k and Bos d 2 after further purification by hydrophobic interaction and anion exchange chromatography. The sizes of relevant MW marker proteins are indicated to the left of each gel.

FIG. 10 shows the amino acid sequence alignment of Can f 4 (as depicted by SEQ ID NO: 2) and Bos d 23k (as depicted by SEQ ID NO: 4).

DETAILED DESCRIPTION OF THE INVENTION

Figure 1:
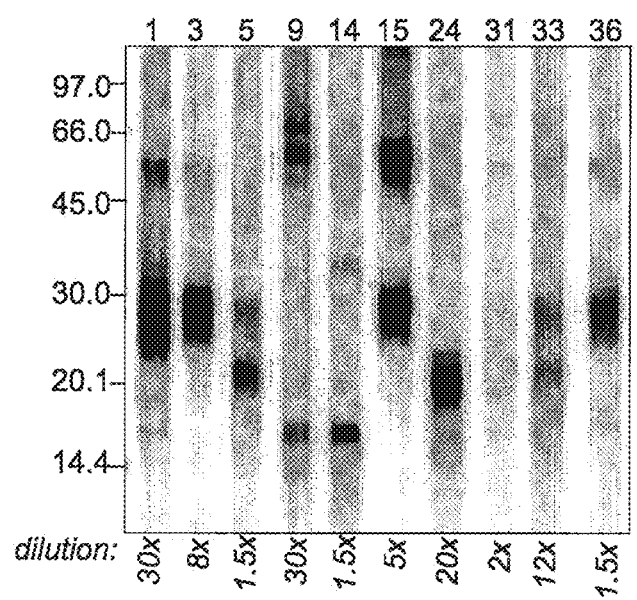
FIG. 1 shows the immunoblot analysis of IgE antibody binding to non-reduced dog dander extract proteins. Ten of 37 sera analysed are shown. Subject number is indicated above and the serum dilution below each lane. The positions of MW marker proteins are indicated to the left.
Figure 2A:
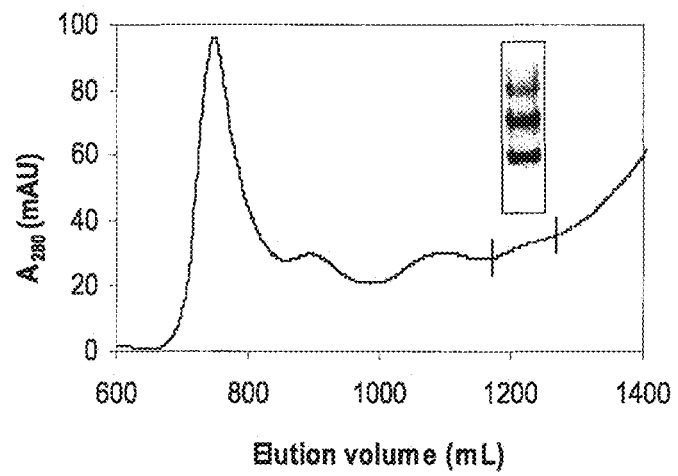
FIGS. 2A-2D show the purification of 16 kDa dog dander protein identified by immunoblotting by four consecutive steps.
Figure 2B:
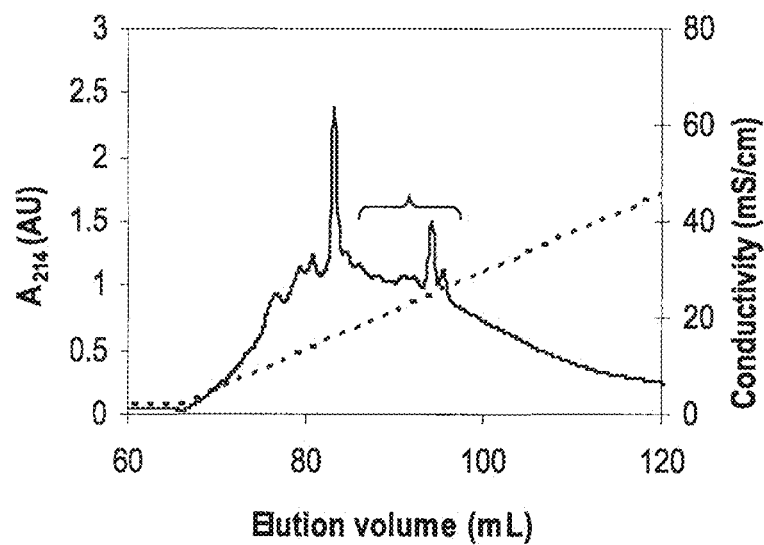
Figure 2C:
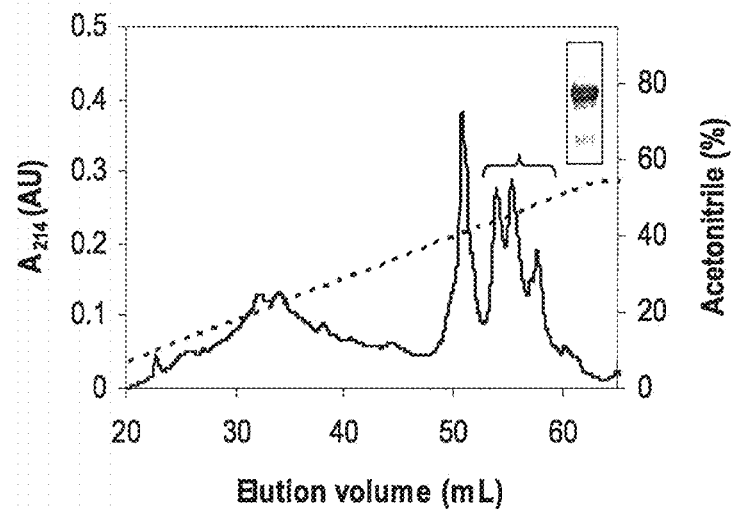
Figure 2D:
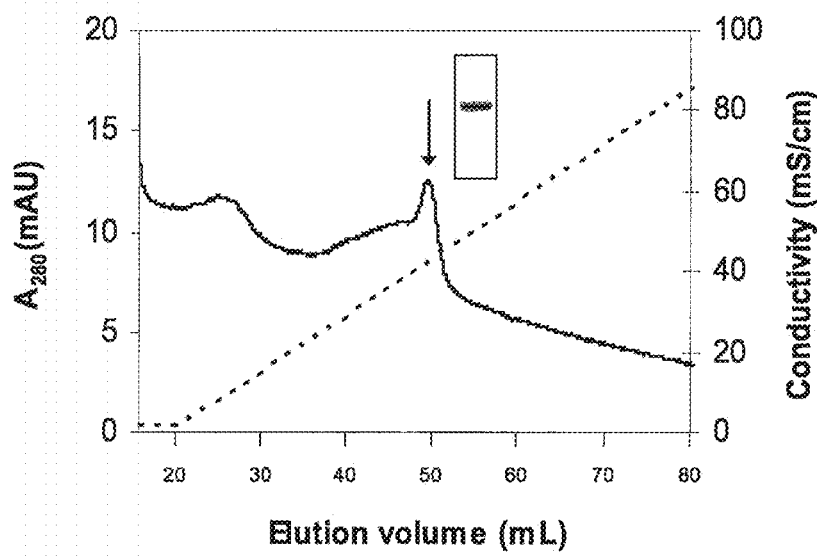

The example below illustrate the present invention with the isolation and use of the lipocalin-like protein Can f 4 from dog. There is also a part illustrating the cross-reactivity between Can f 4 and a cow allergen. The example is only illustrative and should not be considered as limiting the invention, which is defined by the scope of the appended claims.

EXAMPLE

Material and Methods
IgE Immunoblot Analysis

Immunoblot analysis was performed on non-reduced dog dander extract separated by SDS-PAGE using a homogeneous 12.5% ExcelGel (GE Healthcare Life Sciences, Uppsala, Sweden) and electroblotted onto a Hybond ECL nitrocellulose membrane (GE Healthcare Life Sciences). As molecular weight (MW) markers, the LMW kit (GE Healthcare Life Sciences) was used. Protein blots were blocked for 1 h at room temperature using blocking buffer (50 mM phosphate pH 7.4, 0.1% (v/v) Tween-20, 0.9% (w/v) NaCl, 0.3% (w/v) Dextran T10) and then incubated overnight with each patient's serum, diluted 1.5-30-fold in blocking buffer. After washing in blocking buffer with 0.5% (v/v) Tween-20, the membrane was incubated 4 hrs at room temperature with an $^{125}$I-labelled anti-human IgE antibody in blocking buffer and, after washing, bound IgE was radiographically detected using a storage phosphor screen and a Typhoon 9410 Variable Mode Imager (GE Healthcare Life Sciences).

Purification of a 16 kDa Protein from Dog Dander

Dog dander (Allergon, Välinge, Sweden) was extracted in 20 mM MOPS pH 7.6, 0.5 M NaCl (MBS), clarified by centrifugation, filtered through a 0.45 μm mixed cellulose ester filter (Millipore, Billerica, Mass.) and applied to a Superdex 75 column (GE Healthcare Life Sciences) for size exclusion chromatography (SEC). Fractions containing a 16 kDa band observed in immunoblot analysis were concentrated in an Amicon stirred cell (Millipore) using YM-3 filter, desalted on a Sephadex G25 superfine column (GE Healthcare Life Sciences) to 20 mM Tris-HCl pH 8.0. The desalted preparation was then applied to a Source Q column (GE Healthcare Life Sciences) for anion exchange chromatography (AIEC) and eluted with a linear 0-0.5 M NaCl gradient. Further purification was performed by reversed phase chromatography (RPC) using a Source 15 RPC column (GE Healthcare Life. Sciences) and elution with a linear 0-54% gradient of acetonitrile in water containing 0.05% trifluoro acetic acid (TFA). Fractions containing the target protein were identified by SDS PAGE and pooled. Following reduction, alkylation and trypsin cleavage, peptides of the purified protein were isolated by RPC and analysed by amino acid sequencing. For evaluation of IgE antibody binding by ImmunoCAP, the 16 kDa protein was subjected to a final polishing step by cation exchange chromatography (CIEC) using a SP Sepharose FF column (GE Healthcare Life Sciences) equilibrated in 20 mM citrate pH 4.0 and elution with a linear 0-1 M NaCl gradient.

Purification of IgE Binding Proteins from Cow Dander

Cow dander (Allergon) was extracted and fractionated by SEC as described above. Fractions containing a dominant 23 kDa band were pooled, conditioned with NH4SO4 to a final concentration of 1 M and further purified by hydrophobic interaction chromatography (HIC) using a phenyl Sepharose HP column (GE Healthcare Life Sciences). The 23 kDa band eluted in the flow through fraction and was desalted to 20 mM Bis-Tris propane pH 8.5 on a Sephadex G25 superfine column (GE Healthcare Life Sciences) and subsequently applied to a Source 15Q column (GE Healthcare Life Sciences) equilibrated with the same buffer. Elution was performed with a linear 0-0.4 M NaCl gradient and fractions containing the 23 kDa band were pooled. The protein concentration of the final preparation was determined from absorbance at 280 nm, using a calculated extinction coefficient of 1.04 per mg/mL.

Fractions containing a dominant 19 kDa band were pooled and further purified by HIC as described above. The 19 kDa protein was eluted in a linear 0-1 M gradient of NH4SO4 in 20 mM Tris-HCl pH 8.0 and the peak fractions pooled. Desalting and AIEC on a Source 15Q column was performed as described above. The protein concentration of the final preparation was determined from absorbance at 280 nm, using a calculated extinction coefficient of 1.04 per mg/mL.

Protein Analysis

Unless otherwise specified, SDS-PAGE analysis of reduced (4% β-mercaptoethanol) and non-reduced protein samples was performed using a 10% NuPAGE gel (Invitrogen, Carlsbad, Calif.) and Mark12 (Invitrogen) as MW markers. Following electrophoretic separation, proteins were visualized by Coomassie Brilliant Blue staining. N-terminal sequence analysis of extracted protein bands were performed using a Hewlett-Packard G1000A instrument (Hewlett-Packard, Palo Alto, Calif.). Analytical SEC was performed on a Superdex 75 HR 10/30 column (GE Healthcare Life Sciences) equilibrated with MBS. MW calibration of the column was performed using the LMW gel filtration calibration kit (GE Healthcare Life Sciences).

For peptide mass fingerprint (PMF) analysis by matrix assisted laser desorption/ionization time-of-flight (MALDI-TOF) mass spectrometry (MS), sample preparation of RPC-purified protein in solution, including reduction, alkylation and trypsin digestion, was performed essentially as described [10] using a Bruker Dallonics Autoflex 2 instrument (Bruker Daltonics, Bremen, Germany). Tandem MS (MS/MS) analysis was performed to identify selected peptides. To identify proteins matching the PMF and MS/MS results obtained, the MSDB database was searched using a Mascot server (Matrixscience, London, UK).

In-gel trypsin digestion of individual protein bands from SDS-PAGE was performed essentially according to Shevchenko et al. [11] Sample preparation and peptide mass fingerprinting was performed as described above.

Cloning, Expression and Purification of Recombinant Can f 4

Total RNA was prepared from a lateral segment of dog tongue using the RNAqueous kit (Ambion, Austin, Tex.). Polyadenylated RNA was isolated from total RNA using the mRNA Purification kit (GE Healthcare Life Sciences) and first strand cDNA was prepared using the First-Strand cDNA Synthesis kit (GE Healthcare Life Sciences). 3' RACE was performed according to Frohman[12], using the nested forward oligonucleotide primers 5'-ATGAAGATCCTACTGT-TGTGTC-3' (SEQ ID NO: 5) and 5'-CAGCTACCCCTTC-CTAATG-3' (SEQ ID NO: 6), both carrying a terminal NdeI restriction site for cloning. Seven independent 3' RACE clones were isolated and sequenced in their entirety whereby the Can f 4 coding sequence could be defined. DNA sequencing was performed using a an Applied Biosystems 3130 Genetic Analyzer (Applied Biosystems, Foster City, Calif.). DNA and amino acid sequence analyses and calculations were performed using programs of the GCG Wisconsin Package (Accelrys, San Diego, Calif., USA). Signal peptide prediction was performed using SignalP (www.cbs.dtu.dk/services/SignalP). For the purpose of protein expression, the Can f 4 coding sequence was amplified using primers 5'-GTCAGCATATGCAGCTACCCCTTC-CTAATG-3' (SEQ ID NO: 7) and 5'-ACTGACTCGAGT-TCATGGTTGGGACAGTTGTC-3' (SEQ ID NO: 8) and cloned between the NdeI and XhoI sites of vector pET-23a (+) (Novagen, Madison, Wis., USA). Recombinant Can f 4 was produced as a C-terminally hexahistidine tagged protein in *E. coli* BL21, using a 3-L bioreactor (Belach Bioteknik, Solna, Sweden).

For rCan f 4 purification, harvested cells were resuspended in 20 mM Tris-HCl pH 8.0 and lysed by passing the suspension through an Emulsiflex C5 homogenizor (Avestin Inc., Canada) at 15 000-17 000 kPa, After clarification by centrifugation and filtration, the supernatant was applied to a Chelating Sepharose FF column (GE Healthcare Life Sciences), charged with NiSO4. Column washing was performed with 20 mM imidazole in 20 mM Tris-HCl pH 8.0, 0.15 M NaCl and the recombinant protein eluted in a linear 20-500 mM gradient of imidazole in the same buffer. Further purification of the recombinant protein was performed by AIEC in 20 mM Tris-HCl pH 8.0 using a Q Sepharose FF column (GE Healthcare Life Sciences). The protein was eluted using a linear 0-0.5 M NaCl gradient and fractions were pooled according to SDS-PAGE results. The protein concentration of the final preparation was determined from absorbance at 280 nm, using a calculated extinction coefficient of 0.78 per mg/mL. The intactness of the recombinant protein was confirmed by N-terminal sequencing.

Dog Allergic Subjects and Pollen Allergic Controls

Sera from 37 dog allergic subjects from Spain (n=23), Sweden (n=10) and North America (n=4) were used in the study (Table 2). All patients had a doctor's diagnosis of dog allergy, with symptoms such as asthma, rhinoconjunctivitis and urticaria, a positive skin prick test and a positive ImmunoCAP test (Phadia, Uppsala, Sweden) for specific IgE to dog dander extract. For control purposes, sera of 44 pollen allergic subjects without diagnosed or reported symptoms of dog allergy were used. All samples and clinical data were collected under the approval of the local ethics committee at each center.

Specific IgE Antibody Measurements

IgE antibody binding activity of purified recombinant and natural allergens were examined using regular and experimental ImmunoCAP™ tests (Phadia). Experimental ImmunoCAP tests were prepared as described [13]. Assay specificity of experimental tests was assessed using a negative control serum, spiked with myeloma IgE to a final concentration of 0, 1000 or 3000 kU/L. An IgE inhibition experiment was performed by preincubating serum samples with recombinant Can f 4 at a final concentration of 100 µg/mL prior to measurement of IgE antibody binding to the 23 kDa cow dander protein immobilized on ImmunoCAP solid phase. Results were calculated as mean values of duplicate determinations.

Results

Immunoblotting Analysis of Sera from Dog Allergic Subjects

Serum samples from 10 dog allergic subjects were subjected to IgE immunoblot analysis using non-reduced dog dander extract (FIG. 1). For the same sera, ImmunoCAP data on specific IgE to rCan f 1, rCan f 2, nCan f 3 and rCan f 5 were available for comparison. The immunoblot analysis revealed IgE binding to at least 8 different protein bands. Of these, bands in the 23 kDa region correlated with ImmunoCAP IgE binding to rCan f 1 and rCan f 2 (subjects 5, 24, 31 and 33), bands in the 28 kDa region with rCan f 5 reactivity (subjects 1, 3, 5, 15, 31, 33, and 36) and bands at about 60 kDa with nCan f 3 reactivity (subjects 9, 15 and 33).

Immunoblot IgE binding to a 16 kDa band was detected with sera of 4 subjects (1, 9, 14 and 36) of which one (subject 14) gave rise to a particularly intense signal. The fact that this serum showed no IgE binding to any of rCan f 1, rCan f 2, nCan f 3 or rCan f 5 in ImmunoCAP analysis suggested that the 16 kDa band represented a new allergen.

Purification of the 16 kDa Dog Dander Protein Identified by Immunoblotting

A three step purification process comprising SEC followed by AIEC and RPC yielded a preparation of a 16 kDa protein of 90-95% purity (FIG. 2). N-terminal sequence analysis of this protein yielded no reading, suggesting that its N-terminus was blocked. To overcome this problem, the protein was reduced, alkylated and digested with trypsin to generate internal peptides. Four such tryptic peptides could be separated by RPC and analysed by N-terminal sequencing, producing the sequences shown in FIG. 3. BLAST searches with these peptide sequences did not identify an exact match to any known dog protein. However, imperfect matches of peptides 1 and 4 to database entries representing odorant binding proteins from cow and swine suggested that the purified dog protein might be related to this protein family. Further, a TBLASTN search of the dog genome database with peptide 4, using reduced stringency settings, resulted in matches to conceptual translations of three adjacent segments in a terminal region of the X chromosome. PMF analysis of the purified protein did not result in any significant match to a known protein sequence.

The IgE binding activity of the 16 kDa dog dander protein was assessed by ImmunoCAP immunoassay, following a final CIEC polishing step to further increase the purity of the preparation. Sera of 37 dog allergic individuals were analysed and the IgE binding to the purified protein in ImmunoCAP correlated well with the detection of the 16 kDa band in immunoblot analysis of dog dander extract, indicating that the purified protein represented the 16 kDa band observed in immunoblotting.

A Link between Epithelial Allergens from Dog and Cow

Unexpected help towards identification and cloning of the 16 kDa dog allergen came from a separate line of experiments in our laboratory, on epithelial allergens from other animal species. One serum, which was shared between the studies on dog and cow allergens, showed significant IgE antibody binding to both dog and cow dander extract while being non-reactive in ImmunoCAP to all of rCan f 1, rCan f 2, nCan f 3 and rCan f 5, raising the possibility that this serum might define a novel dog allergen.

Figure 8A:
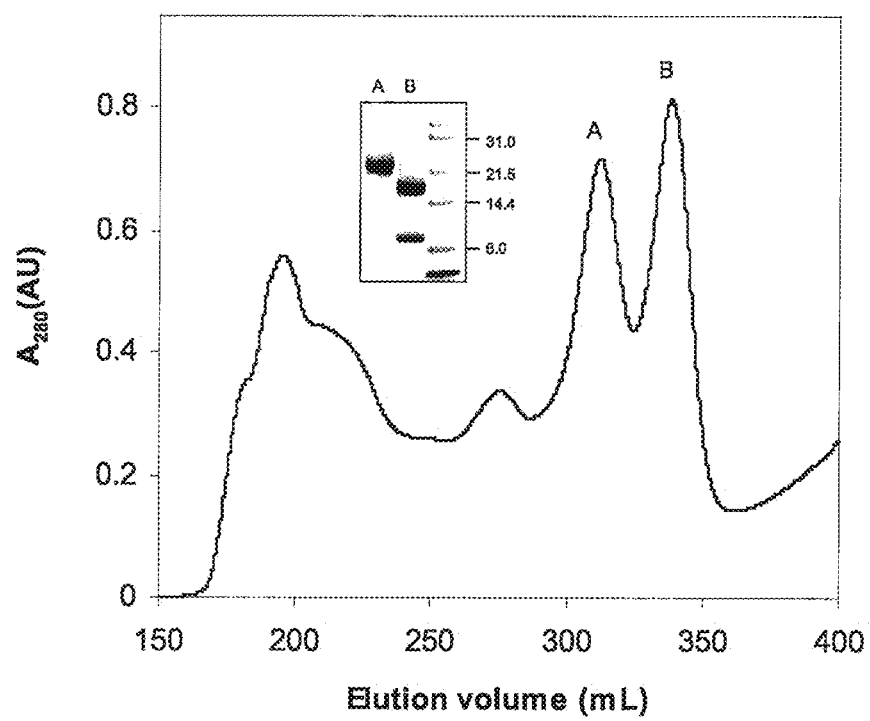
FIGS. 8A-8B shows the purification of two IgE antibody binding proteins, Bos d 23k and Bos d 2, from cow dander.
Figure 8B:
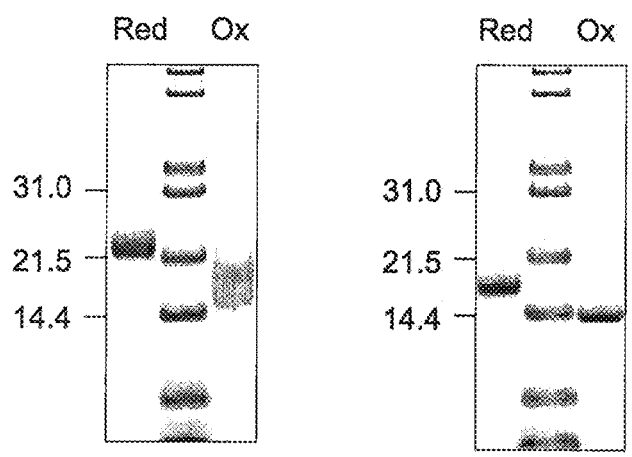

A 23 kDa protein in cow dander extract was found to bind IgE from this serum and could be highly enriched by SEC (FIG. 8, A). The adjacent peak in the SEC fractionation was found to contain the major allergen Bos d 2, a 19 kDa lipocalin, as confirmed by PMF analysis (not shown). Further purification of these proteins by HIC and AIEC (not shown) resulted in highly pure preparations (FIG. 8, B), suitable as immunoassay reagents.

The 23 kDa protein was identified by a significant match ($p<0.05$) of PMF data to database entry XP_581277 (as depicted by SEQ ID NO: 4), representing a bovine lipocalin annotated as "similar to odorant binding protein". Further, N-terminal sequence analysis of the 23 kDa protein revealed the sequence EAQGDASQFT, matching residues 19-28 of the same database entry and thus corroborating the PMF match. This protein is hereafter referred to as Bos d 23k.

Figure 9A:
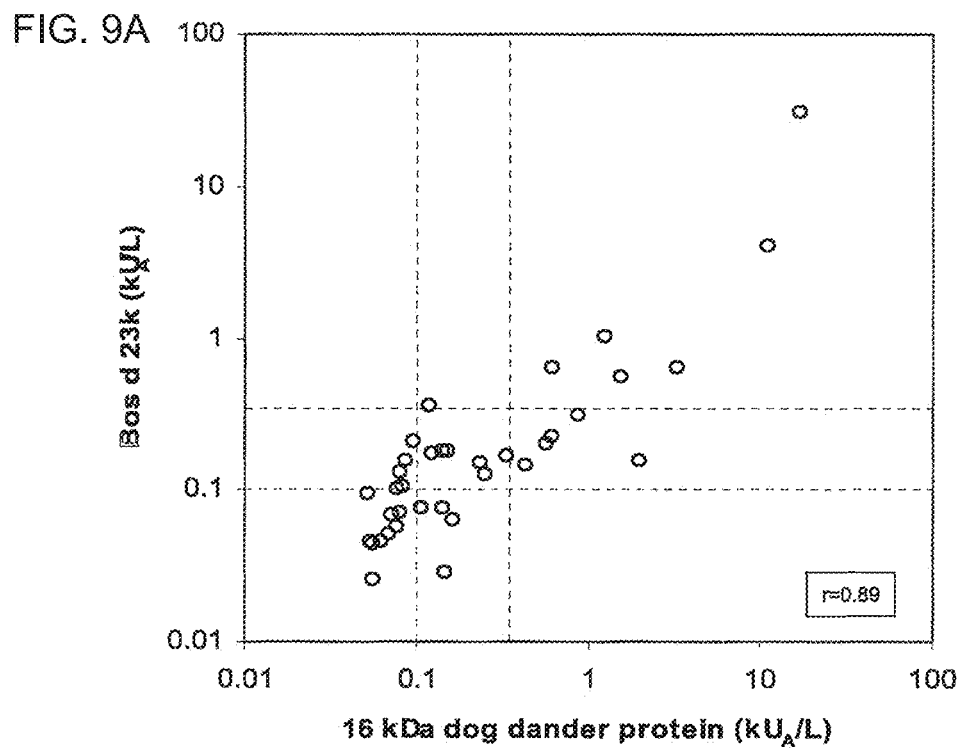
FIGS. 9A-9B show the comparison of IgE antibody binding to Can f 4, Bos d 23k (FIG. 9A) and Bos d 2 (FIG. 9B). The correlation coefficient (r) for each comparison is indicated. Sera from 37 dog allergic subjects were analysed. Hatched lines indicate the 0.10 and 0.35 $kU_A/L$ levels.
Figure 9B:
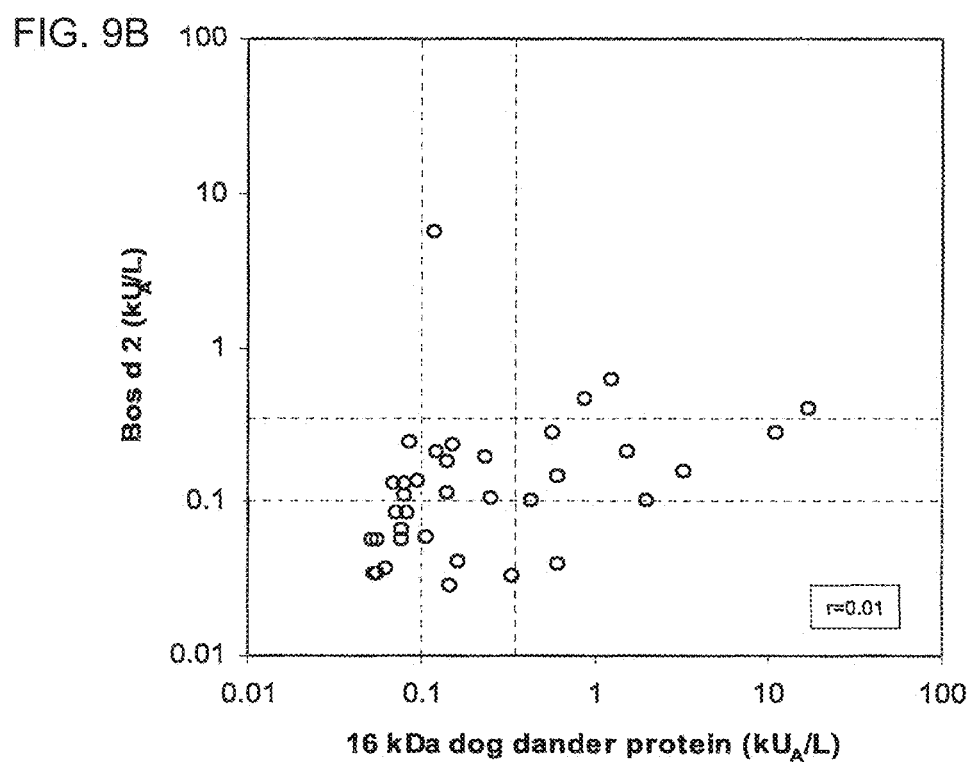

Experimental ImmunoCAP tests prepared with both Bos d 23k and Bos d 2 were used to assess correlation in IgE binding to the 16 kDa dog dander protein. Sera from 37 dog allergic subjects were analysed and the results are shown in FIG. 9. While the 16 kDa dog dander protein and Bos d 2 showed no correlation in IgE binding ($r=0.01$), a significant correlation was observed to Bos d 23k ($r=0.89$), suggesting cross-reactivity and structural similarity between the dog allergen and Bos d 23k.

Cloning and Sequence Analysis of the 16 kDa Dog Dander Protein

Potential sequence similarity between the 16 kDa dog dander protein and Bos d 23k prompted a database search aimed at identifying the dog protein or its gene sequence. A BLASTN search of a dog genome database with the sequence of the bovine protein (XP_581277) resulted in a match to the translation of nucleotide positions 338441-338307 of Acc No. AAEX02025758, a 431454 by segment of the dog genome sequence [14]. Interestingly, the theoretical translation of this genomic region contained a perfect 5-residue match of amino acid residues 9-13 of the reported N-terminal sequence of Can f 4 [9]. Further upstream (339006-338926), a nucleotide sequence encoding amino acids matching residue 1-8 of the Can f 4 sequence, as well as a putative signal peptide, were found.

For the purpose of cloning a cDNA corresponding to the identified segment of AAEX02025758, assumed to encode Can f 4, a 3' RACE experiment was performed. Oligonucleotide primers based on the genomic sequence encoding the first part of the putative signal peptide and a stretch following the predicted cleavage site were used, together with first strand cDNA prepared from poly-A RNA of dog tongue as template. A distinct amplification product was obtained which was cloned, analysed and subsequently used for protein expression experiments.

The complete DNA sequence and amino acid translation of the cloned cDNA is shown in FIG. 4. An open reading frame encoding 174 amino acid residues was identified, of which the first 16 residues were predicted by SignalP to form a signal peptide. The mature protein deduced from the cloned cDNA consisted of 158 amino acid residues, including two cysteines, and had a predicted molecular mass of 17.6 kDa and an isoelectric point of 6.53. To assess the presence of sequence diversity, seven independent 3' RACE clones were isolated and sequenced. A few nucleotide substitutions were found among the clones (not shown) but no one causing variation in amino acid sequence of the protein. In all clones analyzed, the stop codon terminating the open reading frame was followed by a 213-nucleotide untranslated segment preceding a poly-A tract.

The predicted signal peptide cleavage site between residue 16 and 17 would make the glutamine residue at position 17 the first in the mature protein. Consistent with our failure to obtain a sequence reading from the intact protein, an N-terminal glutamine residue may undergo pyroglutamate cyclisation which is known to cause blockage to N-terminal sequencing by Edman degradation (15). Further, upon re-examination of the PMF results for the native protein, a tryptic fragment with a mass of 1759.98 Da was identified, exactly corresponding to that predicted for residue 17-32 of the predicted primary translation product, modified by pyroglutamate cyclisation. In addition, tryptic fragments matching amino acid residues 33-51, 56-63, 66-73 and 95-104 were identified.

The amino acid sequence encoded by the cloned cDNA further contained all four tryptic peptide sequencens obtained from the purified natural 16 kDa protein (FIG. 3), with exact agreement for peptides 2-4 and two conservative amino acid substitutions in peptide 1. In total, protein fragments identified by PMF and peptide sequencing represented a coverage of 58% of the deduced amino acid sequence of Can f 4 (Table 1). Taken together, the results provide strong evidence that the purified 16 kDa allergen and the protein encoded by the cloned cDNA both represent dog allergen Can f 4.

By aligning the cloned cDNA sequence with the genomic sequence of Ace. No. AAEX02025758, the coding part of the Can f 4 gene was found to span a total of 5916 by and comprise 6 exons: 339006-338929 (exon 1), 338447-338307 (exon 2), 335150-335082 (exon 3), 334581-334468 (exon 4), 333609-333511 (exon 5) and 333114-333091 (exon 6). The exact splice point between exons 3 and 4 could not be unambiguously deduced from the sequence and those exon boundaries may instead be 335150-335079 and 334578-334468, respectively.

The amino acid sequences deduced from the Can f 4 cDNA and gene segments deviated from each other at 5 positions. At position 20 of the mature Can f 4 sequence, an isoleucine residue in the cDNA translation corresponded to a valine residue in the gene-derived sequence, at position 30 an aspartic acid residue corresponded to a glutamic acid residue, at position 38 a methionine residue corresponded to a leucine residue, at position 51 a serine residue corresponded to a leucine residue and at position 81 a tyrosine residue corresponded to either an aspartic acid or a cysteine residue, depending on the exact splice point between exons 3 and 4.

In addition to the Can f 4 gene sequence described above, database entry AAEX02025758 was found to contain two other Can f 4 related segments, explaining the three matches obtained in the dog genome TBLASTN search with the tryptic peptide 4 sequence. The three Can f 4 related segments were arranged in tandem at a distance of 5.4 and 6.7 kb from each other, with the one described above located the furthest downstream. The Can f 4 related segment located in the middle had an exon/intron structure similar to that of the Can f 4 gene described above and its deduced amino acid sequence differed at 24 positions as compared to the Can f 4 gene and at 28 positions as compared to the Can f 4 cDNA. Interestingly, it agreed completely with the sequence of tryptic peptide 1 which deviated at two positions from the cDNA-encoded amino acid sequence. In the Can f 4 related segment located furthest upstream, no sequence corresponding to exon 4 could be identified.

Can f 4 belongs to the lipocalin superfamily and displays 38-39% sequence identity to bovine (XP_581277) and porcine [16] (NP_998961) odorant binding proteins. An amino acid sequence alignment of Can f 4 and Bos d 23k is shown in FIG. 10. It can be noted that, apart from a scattered pattern of similar or identical residues, the C-terminal portion of the proteins is highly conserved, as well as both cystein residues (position 62 and 154 in Can f 4). Other conserved elements, characteristic of lipocalins [17], include a GxW motif near the N-terminus (position 13-15), a glycine residue (position 118). Another motif typical of lipocalins [17], YxxxYxG, is present in Bos d 23k (position 74-80) but only partially conserved in Can f 4. Interestingly, despite belonging to the same protein family, Can f 4 showed only 24% and 26% amino acid sequence identity to Can f 1 and Can f 2, respectively.

Production of Recombinant Can f 4

Figure 5A:
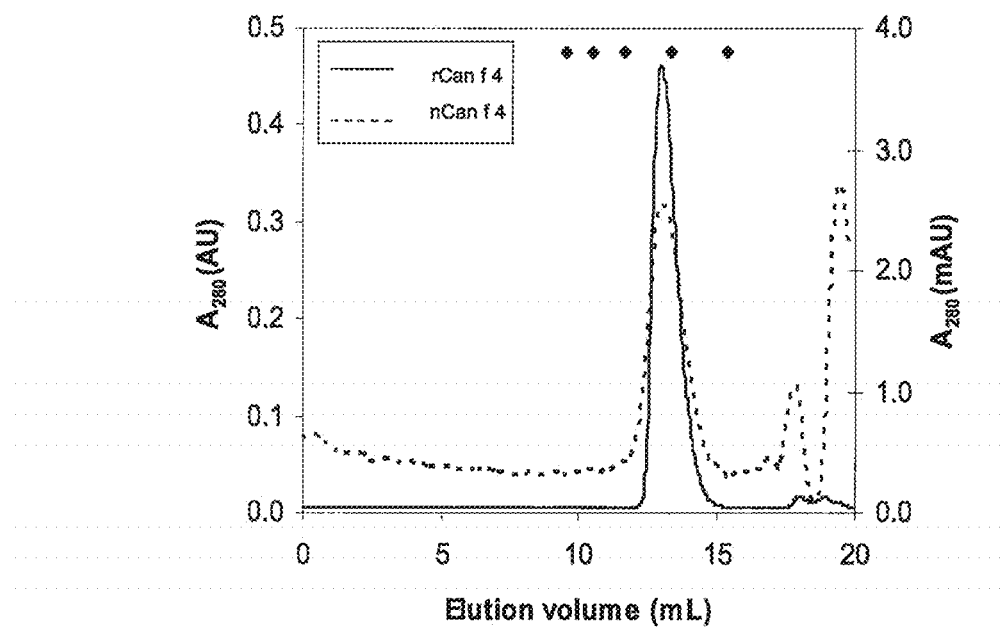
FIGS. 5A-5C show the comparative biochemical and immunological analysis of purified nCan f 4 and rCan f 4.
Figure 5B:
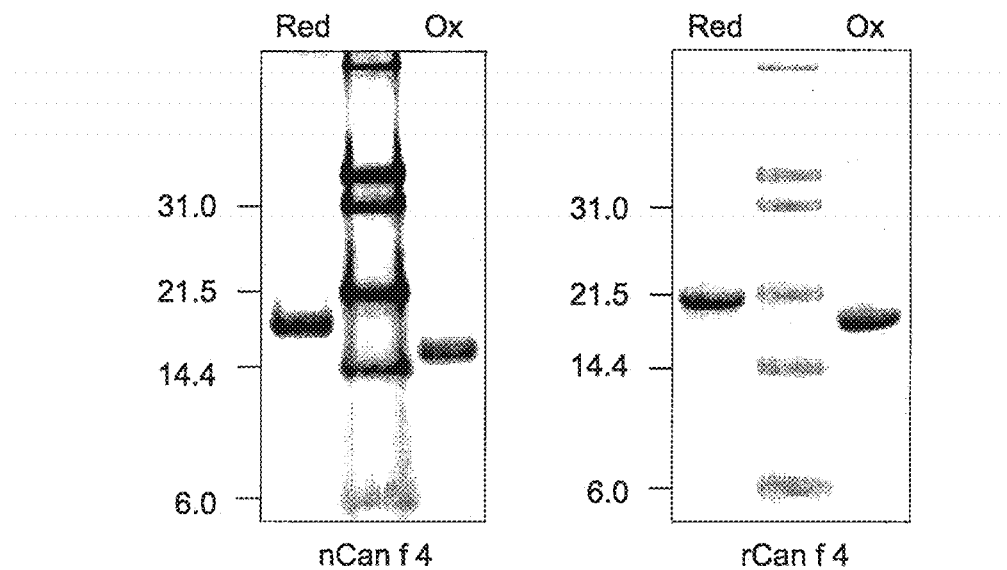
Figure 5C:
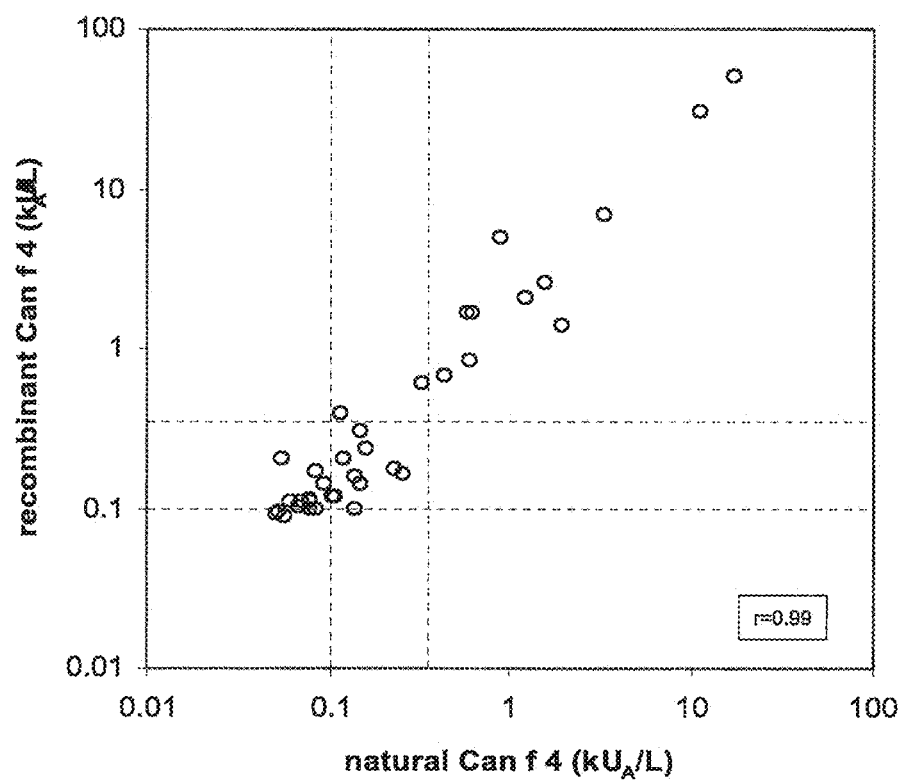

Recombinant Can f 4, excluding the signal peptide, was expressed as a C-terminally hexahistidine tagged protein in *E. coli*. The recombinant protein was purified from the soluble cell fraction by IMAC and AIEC. To assess the aggregation state of the recombinant protein, a sample of the preparation was subjected to analytical SEC, in parallel with natural purified natural Can f 4. As shown in FIG. 5, A, the chromatogram was dominated by a single symmetrical peak in both cases, corresponding to a MW of approximately 16.5 kDa, as defined by the calibrators used. In SDS-PAGE (FIG. 5, B), both natural and recombinant Can f 4 exhibited a shift in migration rate upon reduction, suggesting that the two cystein residues present in the protein were engaged in a disulfide bridge. It should be noted that the apparent molecular weight of Can f 4 indicated by the initial immunoblot analysis (FIG. 1) was affected by the fact the dog dander extract used for the analysis was applied to the separation gel in a non-reduced form, leading to an underestimation in relation to the size of the protein indicated by subsequent analyses of reduced samples of the purified protein. The size increment displayed by rCan f 4 in comparison to the natural protein was consistent with the addition of a C-terminal hexahistidine tag in the recombinant protein and the nearly complete retention of the initiator methionine residue.

Analysis of Specific IgE Antibody Binding to rCan f 4 in Dog Allergic Subjects

The immunological activity of recombinant Can f 4 was assessed in comparison to the natural protein, purified from dog dander. Each protein was immobilized on ImmunoCAP™ solid phase and their IgE antibody binding examined using serum samples from 37 dog allergic subjects (FIG. 5, C). The two datasets showed a very strong correlation (r=0.99), demonstrating that the recombinant allergen closely resembled its natural counterpart with respect to IgE antibody binding determinants.

Figure 6:
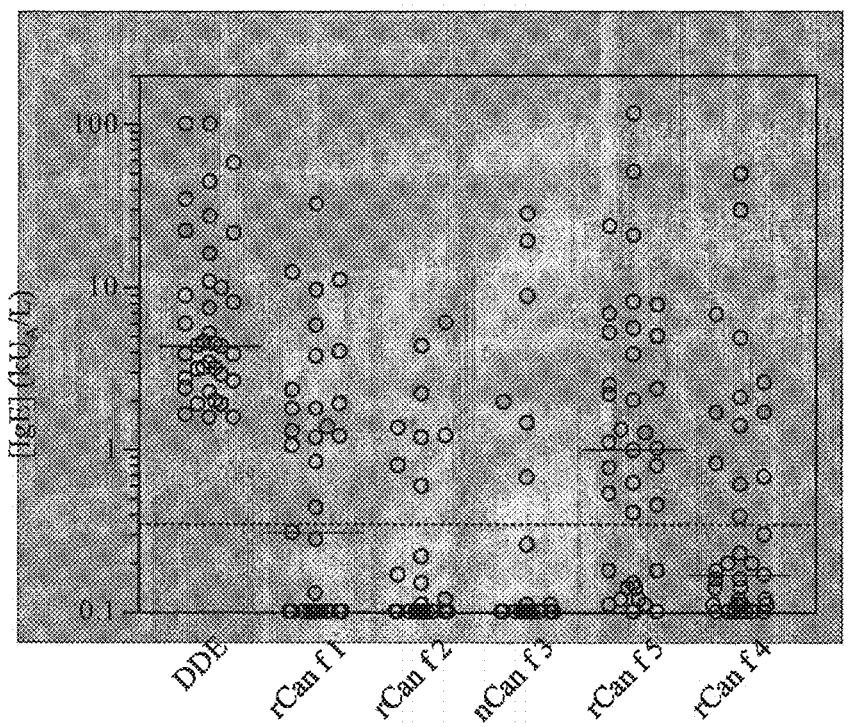
FIG. 6 shows the concentration of IgE antibodies to dog dander extract (DDE), rCan f 1, rCan f 2, nCan f 3, rCan f 5 and rCan f 4 among 37 dog allergic subjects. Horizontal bars indicate median values. Dotted line indicates the 0.35 $kU_A/L$ level. Values below 0.1 $kU_A/L$ were set to 0.1 $kU_A/L$.

The frequency and magnitude of IgE antibody reactivity to Can f 4 in comparison to other dog dander allergens is illustrated in FIG. 6. A more comprehensive dataset on the dog allergic subjects and their sensitization pattern is present in Table 2. Among the 37 sera analysed, 13 (35%) displayed IgE antibody binding to Can f 4. One of the 13 Can f 4 reactive sera showed IgE binding to none of the other dog allergens tested. No correlation in IgE binding could be observed between Can f 4 and Can f 1 or Can f 2, consistent with their highly divergent primary structure. Assay specificity of the experimental Can f 4 ImmunoCAP test was demonstrated by the low results obtained upon testing a negative control serum spiked with up to 3000 kU/L of myeloma IgE (Table 3).

To examine the occurrence of Can f 4 specific IgE antibody in atopic individuals not allergic to dog, sera of 44 pollen allergic subjects without diagnosed or reported symptoms of dog allergy were tested with all dog allergen components available and a range of pollen extracts (Table 4). Seven of those sera (16%) showed a positive response to dog dander extract, with one exception at levels of 2 $kU_A$/L or below, one of which also showed IgE antibody binding to rCan f 4. No serum negative to dog dander showed a positive response to rCan f 4.

Cross-Reactivity between rCan f 4 and Bos d 23k

Figure 7:
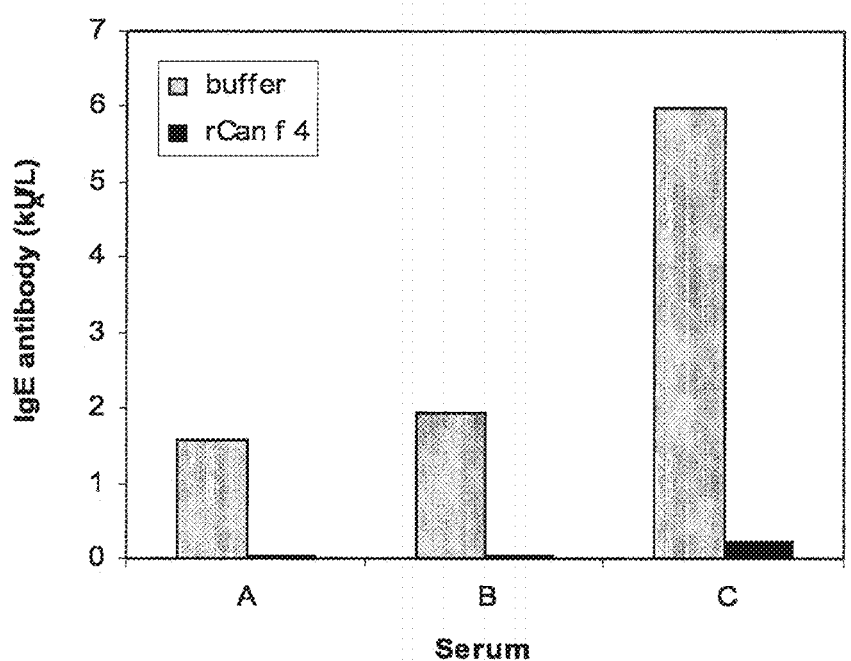
FIG. 7 shows the inhibition of IgE antibody binding to Bos d 23k by rCan f 4. Three Bos d 23k-reactive sera (A-C) were preincubated with 100 μg/mL rCan f 4 (black bars) of buffer (negative control, gray bars), prior to measurement of IgE binding to immobilized Bos d 23k.

To study the extent of cross-reactivity between Can f 4 and Bos d 23k indicated by their correlation in IgE antibody binding, an IgE inhibition experiment was performed with three sera reactive to the bovine protein. The purified bovine protein was attached to ImmunoCAP solid phase and IgE binding from sera preincubated either with rCan f 4 or buffer was measured. As can be seen in FIG. 7, rCan f 4 almost completely (≥96%) inhibited the IgE binding to the cow dander protein in all three sera, demonstrating that all determinants of IgE binding to the bovine protein recognised by the sera used in the experiment were shared with rCan f 4.

Discussion

As described in this application, we have isolated, cloned and characterized a IgE binding protein from dog dander identified as Can f 4. Prior to this work, only a 13-residue N-terminal sequence of this allergen was known. Can f 4 was found to belong to the diverse lipocalin superfamily and showed similarity to odorant binding proteins of other species, including cow and swine. Can f 4 was found to cross-react with a 23 kDa odorant binding protein purified from cow dander.

Purification of natural Can f 4 resulted in a very poor yield due to both scarcity of the protein in the dander extract and low chromatographic resolution. The presence of Can f 4 in several peaks in RPC and the broad Can f 4 peak in the CIEC step indicated some degree of heterogeneity of the protein. While several explanations for this behaviour are possible, including protein modification, partial degradation and the presence of isoforms, N-linked glycosylation is not likely as the sequence of Can f 4 contained no potential site for N-glycan attachment. Among the four tryptic peptide sequences obtained, one showed deviations at two positions as compared to the amino acid sequence deduced from the cDNA clones and the genomic segment identified. Thus, it is possible that isoform variation may have contributed to the heterogeneity observed during purification of the natural protein, even though no evidence of sequence variability was obtained in the DNA sequencing of seven independent cDNA clones. Additionally, tryptic fragment sequencing and MALDI-TOF analysis together confirmed 58% of the amino acid sequence deduced from the cDNA clones, suggesting limited polymorphism. Even if it cannot be exclude that at least one of the additional Can f 4 related genomic segments identified is expressed and may give rise to a variant form of Can f 4, our only indication of that was the matching of two amino acid residues of tryptic fragment 1 that deviated from the cDNA-encoded sequence. No other peptide sequence matched preferentially to the other Can f 4 related segment and all cDNA clones were clearly derived from the Can f 4 gene for which the nucleotide positions are detailed in this application.

Regardless of possible isoform variation, the recombinant form of Can f 4 produced displayed excellent agreement with the purified natural protein, both biochemically and immunologically. The two proteins eluted at exactly the same volume in analytical SEC and their IgE antibody binding showed a very high correlation. Most importantly, no case of IgE binding to the natural but not to the recombinant allergen was observed. In fact, somewhat higher IgE binding was observed to the experimental tests carrying the recombinant protein but this was most likely due to a lower than optimal coupling concentration of the natural protein, forced by the poor purification yield.

The importance of Can f 4 as a dog dander allergen was assessed by ImmunoCAP testing of sera from 37 dog allergic subjects. In a recent study involving the same population, we reported that 49% displayed IgE antibody binding to Can f 1, 22% to Can f 2, 16% to Can f 3 and 70% to Can f 5. In this work, we found that 13 of the 37 subjects (35%) were sensitized to Can f 4. Thus, Can f 4 was more commonly recognized than both rCan f 2 and nCan f 3, which appeared as minor allergens in this study population. Of the 13 Can f 4 reactive sera, one showed IgE binding to none of the other dog allergens tested, suggesting that Can f 4 may be relevant as an independent sensitizer in dog allergy and an important addition to component-resolved diagnostics. This notion is underpinned by the uniqueness of Can f 4 both in sequence and IgE binding as compared to Can f 1 and Can f 2. The fact that only one of 44 pollen allergic controls without dog allergy showed a weak IgE antibody response to Can f 4 suggested that IgE recognition of this allergen does not frequently occur as a result of other aeroallergen sensitizations.

In comparison to dog dander extract, cow dander extract appeared to contain much higher amounts of allergens and therefore gave more satisfactory purification results. Judging from SDS-PAGE analysis of cow dander extract, the dominant proteins in the 10-40 kDa range were Bos d 2 and the 23 kDa protein reported here (Bos d 23k), seemingly being present in similar amounts. Bos d 2 has been well established as a major allergen in cow dander, produced as a recombinant allergen and structurally characterized [18-22]. In contrast, much less is known about Bos d 23k, although it may be identical to a previously reported IgE-binding, 22 kDa protein band revealed by immunoblot analysis of cow dander extract [21-23]

The 154-residue amino acid sequence of Bos d 23k predicted a molecular mass of 17.8 kDa, almost exactly the same as that of Can f 4. Despite this fact, it showed significantly slower migration rate than Can f 4 in SDS-PAGE. As the two proteins are related in sequence and may be assumed to have a similar fold, a difference in glycosylation would be a likely explanation for the observed electrophoretic disparity. Indeed, inspection of the sequences reveals that Bos d 23k contains a potential N-glycosylation site at asparagine residue 45 of the mature protein whereas none is present in the sequence of Can f 4.

Among known dog and cow dander allergens, serum albumin (Can f 3 and Bos d 6, respectively) represents the only well recognised cross-reactivity to allergens of other species. The cross reactivity between Can f 4 and Bos d 23k thus provides a novel immunological association between dog and cow dander allergens. Given their relatively low level of overall sequence identity, 37%, the extensive cross-reactivity between the two proteins appears somewhat surprising. However, it is possible that the observed cross-reactivity is due to portions of the proteins having higher sequence similarity than the overall score. In particular, the C-terminal part of the two proteins is significantly conserved, with the 20-residue segment between position 136/133 and 155/152 showing 75% identity. Despite the demonstrable cross-reactivity between the two proteins, the IgE response was higher to Can f 4 than to Bos d 23k for all sera tested, implying that Can f 4 rather than Bos d 23k was the primary sensitizer in our study population.

In conclusion, this application reports the cloning and characterization of dog allergen Can f 4. Recombinant Can f 4 will be important in component resolved diagnostics in dog allergy and its cross-reactivity with a highly abundant bovine dander protein raises the possibility of a linkage between allergy to dog and cow dander.

TABLE 1

Can f 4 protein fragment identification
Amino acid residue position*

| Peptide sequence | MALDI-TOF |
|---|---|
| 28-39 | 1-16 |
| 79-88 | 17-35 |
| 120-130 | 40-47 |
| 139-153 | 50-57 |
|  | 79-88 |

*Position referring to mature protein sequence

TABLE 2

Dog allergic subjects: demographics, allergy symptoms and dog allergen sensitization*

| Subject No. | Age | Country | Symptoms | e5 | rCan f 1 | rCan f 2 | nCan f 3 | rCan f 5 | rCan f 4 |
|---|---|---|---|---|---|---|---|---|---|
| 1 | 35 | ES | A, RC | >100 | 0.09 | 0.12 | 0.08 | >100 | 26.7 |
| 2 | 43 | ES | A, RC | 5.9 | 0.28 | 0.06 | 0.05 | 5.3 | 0.11 |
| 3 | 43 | ES | A, RC | 16.0 | 0.05 | 0.07 | 0.05 | 23.6 | 0.14 |
| 4 | 37 | ES | A, RC | 5.2 | 0.13 | 0.05 | 0.06 | 0.11 | 0.23 |
| 5 | 25 | ES | A, RC | 3.1 | 1.92 | 0.17 | 0.07 | 0.41 | 0.18 |
| 6 | 41 | ES | A, RC | 4.3 | 0.00 | 0.01 | 0.03 | 2.5 | 0.68 |

TABLE 2-continued

Dog allergic subjects: demographics, allergy symptoms and dog allergen sensitization*

| Subject No. | Age | Country | Symptoms | e5 | rCan f 1 | rCan f 2 | nCan f 3 | rCan f 5 | rCan f 4 |
|---|---|---|---|---|---|---|---|---|---|
| 7 | 39 | ES | RC | 2.8 | 0.00 | 0.01 | 0.02 | 2.0 | 0.20 |
| 8 | 42 | ES | RC | 1.6 | 0.00 | 0.02 | 0.04 | 0.62 | 0.10 |
| 9 | 19 | ES | RC | >100 | 11.0 | 2.2 | 28.2 | 0.18 | 49.5 |
| 10 | 19 | ES | RC | 2.0 | 0.08 | 0.11 | 0.11 | 1.0 | 4.9 |
| 11 | 34 | ES | RC | 9.9 | 0.01 | 0.02 | 0.02 | 7.8 | 0.11 |
| 12 | 42 | ES | RC | 3.4 | 1.2 | 0.02 | 0.01 | 0.14 | 0.10 |
| 13 | 51 | ES | A, RC | 1.6 | 3.8 | 0.00 | 0.01 | 0.15 | 0.09 |
| 14 | 26 | ES | RC | 2.3 | 0.04 | 0.03 | 0.02 | 0.09 | 1.4 |
| 15 | 44 | ES | RC | 10.8 | 0.03 | 0.02 | 19.1 | 8.1 | 0.10 |
| 16 | 21 | ES | RC | 4.6 | 0.02 | 0.01 | 0.04 | 2.2 | 0.11 |
| 17 | 39 | ES | A, RC | 34.8 | 0.02 | 0.02 | 1.4 | 20.8 | 1.7 |
| 18 | 32 | ES | RC | 2.4 | 1.1 | 0.02 | 0.01 | 1.3 | 0.10 |
| 19 | 23 | ES | RC | 8.8 | 0.00 | 0.01 | 0.01 | 6.8 | 0.09 |
| 20 | 23 | ES | A, RC | 21.5 | 5.8 | 0.07 | 8.8 | 0.99 | 0.16 |
| 21 | 37 | ES | A, RC | 3.2 | 0.04 | 0.01 | 0.03 | 2.4 | 0.30 |
| 22 | 22 | ES | A, RC | 57.5 | 12.2 | 0.22 | 0.26 | 50.7 | 6.8 |
| 23 | 23 | ES | RC, U | 8.1 | 2.3 | 0.05 | 0.11 | 0.10 | 0.10 |
| 24 | 50 | SE | RC | 44.5 | 32.1 | 0.15 | 0.08 | 0.14 | 0.16 |
| 25 | 44 | SE | A, RC | 27.1 | 9.6 | 4.4 | 0.11 | 5.0 | 2.1 |
| 26 | 25 | SE | RC | 2.7 | 1.2 | 0.60 | 0.67 | 0.11 | 0.12 |
| 27 | 29 | SE | A, RC | 1.9 | 0.31 | 0.07 | 0.06 | 0.54 | 0.82 |
| 28 | 27 | SE | RC | 3.9 | 1.4 | 0.09 | 0.08 | 0.77 | 0.17 |
| 29 | 32 | SE | U | 4.4 | 1.8 | 1.2 | 0.08 | 0.18 | 0.39 |
| 30 | 25 | SE | RC | 3.2 | 0.01 | 0.02 | 0.08 | 1.3 | 0.11 |
| 31 | 52 | SE | A | 3.8 | 0.44 | 1.2 | 0.05 | 0.46 | 0.11 |
| 32 | 20 | SE | A, RC | 7.4 | 1.8 | 1.4 | 0.04 | 3.8 | 2.6 |
| 33 | 29 | SE | A, RC | 22.1 | 4.0 | 6.1 | 2.0 | 5.6 | 1.7 |
| 34 | 32 | NA | RC | 2.9 | 0.84 | 0.06 | 0.08 | 0.12 | 0.12 |
| 35 | 30 | NA | RC | 4.5 | 1.3 | 0.05 | 0.05 | 0.80 | 0.20 |
| 36 | 48 | NA | A, RC | 1.9 | 0.00 | 0.01 | 0.01 | 1.1 | 0.61 |
| 37 | 27 | NA | RC | 1.6 | 0.09 | 0.80 | 0.06 | 0.12 | 0.14 |

ES, Spain;
NA, North America;
SE, Sweden;
e5, dog dander extract;
RC, rhinoconjunctivitis;
A, asthma;
U, urticaria
*Allergen specific IgE antibody in international kilounits per litre; negative: less than 0.35 $kU_A/L$

TABLE 3

Assay specificity of experimental rCan f 4 ImmunoCAP test

| Test sample | Test result* |
|---|---|
| Negative serum | 0.002 |
| Negative serum + 1000 KU/L myeloma IgE | 0.023 |
| Negative serum + 3000 KU/L myeloma IgE | 0.124 |

*Allergen specific IgE antibody in international kilounits per litre; negative: less than 0.35 $kU_A/L$

TABLE 4

Pollen allergic subjects without diagnosed or reported symptoms of dog allergy: demographics, and allergen sensitization*

| Subject | Country | e5 | rCan f 1 | rCan f 2 | nCan f 3 | rCan f 5 | rCan f 4 | t3 | t9 | g6 | w21 | w6 |
|---|---|---|---|---|---|---|---|---|---|---|---|---|
| 1 | DE | 0.20 | 0.01 | 0.01 | 0.01 | 0.02 | 0.01 | 3.7 | 1.3 | 81.8 | 0.12 | 0.39 |
| 2 | DE | 0.03 | 0.00 | 0.01 | 0.00 | 0.01 | 0.00 | 0.01 | 0.17 | 14.0 | 0.03 | 0.11 |
| 3 | DE | 0.03 | 0.00 | 0.01 | 0.01 | 0.01 | 0.00 | 0.16 | 0.26 | 0.39 | 0.25 | 0.20 |
| 4 | DE | 0.04 | 0.00 | 0.01 | 0.00 | 0.02 | 0.02 | 0.01 | 0.20 | 12.5 | 0.05 | 0.05 |
| 5 | DE | 0.01 | 0.00 | 0.00 | 0.01 | 0.00 | 0.00 | 1.3 | 1.7 | 2.2 | 0.03 | 0.66 |
| 6 | DE | 0.22 | 0.00 | 0.00 | 0.00 | 0.15 | 0.00 | 0.02 | 0.37 | 15.1 | 0.05 | 0.12 |
| 7 | ES | 0.02 | 0.01 | 0.01 | 0.01 | 0.02 | 0.00 | 0.00 | 0.00 | 12.6 | 0.00 |
| 8 | ES | 42.3 | 1.2 | 0.07 | 8.4 | >100 | 0.05 | 0.05 | 4.0 | 9.5 | 0.29 | 0.17 |
| 9 | ES | 0.14 | 0.03 | 0.02 | 0.05 | 0.02 | 0.03 | 2.7 | 6.5 | 25.2 | 10.0 | 3.0 |
| 10 | ES | 0.01 | 0.02 | 0.00 | 0.00 | 0.01 | 0.00 | 0.00 | 3.7 | 0.00 | 0.01 | 0.00 |
| 11 | ES | 0.08 | 0.01 | 0.02 | 0.05 | 0.02 | 0.02 | 0.01 | 1.3 | 39.3 | 2.1 | 0.14 |
| 12 | ES | 0.05 | 0.01 | 0.01 | 0.01 | 0.01 | 0.00 | 0.18 | 0.16 | 0.60 | 7.9 | 0.11 |
| 13 | ES | 0.06 | 0.01 | 0.01 | 0.01 | 0.02 | 0.01 | 4.9 | 8.0 | 31.6 | 1.7 | 3.0 |

TABLE 4-continued

Pollen allergic subjects without diagnosed or reported symptoms of dog allergy: demographics, and allergen sensitization*

| Subject | Country | e5 | rCan f 1 | rCan f 2 | nCan f 3 | rCan f 5 | rCan f 4 | t3 | t9 | g6 | w21 | w6 |
|---|---|---|---|---|---|---|---|---|---|---|---|---|
| 14 | ES | 0.11 | 0.00 | 0.01 | 0.01 | 0.08 | 0.01 | 0.09 | 8.6 | 16.6 | 0.91 | 0.93 |
| 15 | ES | 0.30 | 0.00 | 0.01 | 0.01 | 0.02 | 0.01 | 0.01 | 0.04 | 0.01 | 30.9 | 0.01 |
| 16 | ES | 0.01 | 0.00 | 0.00 | 0.00 | 0.01 | 0.00 | 0.00 | 0.01 | 0.00 | 0.88 | 0.00 |
| 17 | ES | 0.07 | 0.00 | 0.00 | 0.01 | 0.01 | 0.00 | 0.00 | 0.00 | 0.00 | 15.7 | 0.00 |
| 18 | ES | 0.09 | 0.00 | 0.00 | 0.00 | 0.01 | 0.01 | 0.01 | 11.8 | 0.06 | 0.05 | 0.00 |
| 19 | ES | 0.05 | 0.00 | 0.01 | 0.01 | 0.01 | 0.02 | 0.24 | 0.82 | 25.1 | 0.37 | 0.31 |
| 20 | ES | 0.01 | 0.00 | 0.00 | 0.00 | 0.01 | 0.00 | 0.00 | 7.2 | 5.2 | 0.02 | 0.00 |
| 21 | ES | 0.00 | 0.00 | 0.00 | 0.00 | 0.00 | 0.00 | 0.07 | 0.15 | 0.00 | 6.6 | 0.00 |
| 22 | ES | 0.01 | 0.00 | 0.00 | 0.00 | 0.00 | 0.00 | 0.04 | 0.13 | 0.38 | 20.4 | 0.38 |
| 23 | ES | 0.03 | 0.00 | 0.00 | 0.00 | 0.01 | 0.00 | 0.07 | 3.1 | 0.04 | 0.13 | 0.00 |
| 24 | ES | 0.05 | 0.00 | 0.00 | 0.00 | 0.01 | 0.02 | 0.00 | 0.98 | 41.1 | 0.03 | 0.11 |
| 25 | ES | 0.01 | 0.00 | 0.00 | 0.00 | 0.00 | 0.00 | 0.37 | 11.2 | 0.02 | 11.0 | 0.00 |
| 26 | ES | 1.1 | 0.00 | 0.00 | 0.00 | 1.3 | 0.00 | 2.2 | 18.9 | 0.01 | 51.9 | 0.03 |
| 27 | ES | 0.24 | 0.03 | 0.04 | 0.03 | 0.04 | 0.05 | 0.05 | 5.0 | 3.0 | 0.10 | 0.04 |
| 28 | ES | 0.01 | 0.00 | 0.00 | 0.00 | 0.01 | 0.00 | 0.01 | 0.02 | 0.01 | 5.0 | 0.05 |
| 29 | ES | 0.10 | 0.01 | 0.02 | 0.02 | 0.01 | 0.02 | 0.26 | 4.7 | 80.3 | 0.44 | 4.0 |
| 30 | ES | 0.01 | 0.00 | 0.00 | 0.00 | 0.00 | 0.00 | 0.01 | 7.1 | 4.4 | 0.45 | 0.01 |
| 31 | ES | 0.02 | 0.00 | 0.01 | 0.00 | 0.01 | 0.00 | 0.05 | 51.2 | 0.07 | 0.07 | 0.17 |
| 32 | ES | 1.0 | 0.00 | 0.00 | 0.00 | 1.1 | 0.00 | 0.00 | 1.7 | 0.02 | 0.05 | 0.00 |
| 33 | ES | 0.06 | 0.02 | 0.01 | 0.01 | 0.02 | 0.00 | 0.12 | 37.4 | 1.9 | 0.26 | 0.16 |
| 34 | ES | 0.01 | 0.00 | 0.00 | 0.00 | 0.01 | 0.00 | 0.02 | 0.06 | 0.51 | 1.6 | 0.00 |
| 35 | ES | 0.01 | 0.02 | 0.01 | 0.00 | 0.01 | 0.01 | 0.02 | 0.86 | 6.4 | 3.0 | 0.03 |
| 36 | ES | 2.0 | 0.00 | 0.00 | 0.00 | 2.0 | 0.00 | 0.01 | 0.36 | 6.6 | 0.03 | 0.02 |
| 37 | ES | 1.9 | 1.5 | 1.2 | 2.0 | 0.58 | 0.95 | 51.2 | >100 | >100 | >100 | 74.7 |
| 38 | ES | 0.01 | 0.00 | 0.00 | 0.00 | 0.00 | 0.00 | 0.02 | 0.12 | 0.21 | 12.3 | 0.00 |
| 39 | ES | 0.64 | 0.02 | 0.03 | 0.03 | 0.61 | 0.03 | 1.6 | 3.8 | 1.8 | 77.8 | 0.88 |
| 40 | ES | 0.00 | 0.00 | 0.00 | 0.00 | 0.00 | 0.00 | 0.01 | 0.30 | 0.00 | 0.02 | 0.00 |
| 41 | ES | 0.09 | 0.00 | 0.00 | 0.00 | 0.07 | 0.00 | 0.01 | 5.0 | 0.00 | 0.02 | 0.00 |
| 42 | ES | 0.00 | 0.00 | 0.00 | 0.00 | 0.00 | 0.00 | 0.01 | 5.6 | 0.00 | 0.03 | 0.00 |
| 43 | ES | 1.2 | 0.04 | 0.07 | 0.06 | 0.06 | 0.04 | 0.14 | 6.0 | 9.1 | 14.8 | 0.12 |
| 44 | ES | 0.06 | 0.04 | 0.01 | 0.01 | 0.02 | 0.01 | 0.03 | 0.46 | 14.0 | 0.18 | 0.38 |

ES, Spain;
DE, Germany;
e5, dog dander extract;
t3, birch pollen extract;
t9, olive pollen extract;
g6, timothy grass pollen extract;
w21, *Parietaria judaica* pollen extract;
w6, mugwort pollen extract
*Allergen specific IgE antibody in international kilounits per litre; negative: less than 0.35 $kU_A/L$

TABLE 5

| Content of sequence listing | |
|---|---|
| SEQ ID NO | Sequence |
| SEQ ID NO: 1 | Can f 4 DNA |
| SEQ ID NO: 2 | Can f 4 protein |
| SEQ ID NO: 3 | Bos d 23k DNA |
| SEQ ID NO: 4 | Bos d 23k protein |

REFERENCES

1. Custovic A, Green R, Taggart S C O, Smith A, Pickering C A C, Chapman M D, et al. Domestic allergens in public places II: dog (Can f 1) and cockroach (Bla g 2) allergens in dust and mite, cat, dog and cockroach allergens in the air in public buildings. Clinical and Experimental Allergy 1996; 26:1246-52.
2. Spitzauer S. Allergy to mammalian proteins: At the borderline between foreign and self? International Archives of Allergy and Immunology 1999; 120:259-69.
3. Spitzauer S, Schweiger C, Anrather J, Ebner C, Scheiner O, Kraft D, et al. Characterisation of dog allergens by means of immunoblotting. International Archives of Allergy and Immunology 1993; 100:60-7.
4. Konieczny A, Morgenstern J P, Bizinkauskas C B, Lilley C H, Brauer A W, Bond J F, et al. The major dog allergens, Can f 1 and Can f 2, are salivary lipocalin proteins: cloning and immunological characterization of the recombinant forms. Immunology 1997; 92:577-86.
5. Mattsson L, Lundgren T, Everberg H, Larsson H, Lidholm J. Prostatic kallikrein: a new major dog allergen. J Allergy Clin Immunol 2009; 123:362-8.
6. Yman L, Brandt R, Ponterius G. Serum albumin—an important allergen in dog epithelia extracts. Int Arch Allergy Appl Immunol 1973; 44:358-68.
7. de Groot H, Goei KGH, van Swieten P, Aalberse RC. Affinity purification of a major and a minor allergen from dog extract: Serologic activity of affinity-purified Can f I and of Can f I-depleted extract. Journal of Allergy and Clinical Immunology 1991; 87:1056-65.
8. Boutin Y, Hébert H, Vrancken E R, Mourad W. Allergenicity and cross-reactivity of cat and dog allergenic extracts. Clinical Allergy 1988; 18:287-93.
9. Saarelainen S, Taivainen A, Rytkönen-Nissinen M, Auriola 5, Immonen A, Mäntyjärvi R, et al. Assessment of recombinant dog allergens Can f 1 and Can f 2 for the diagnosis of dog allergy. Clinical and Experimental Allergy 2004; 34:1576-82.
10. Movérarc R, Everberg H, Carlsson R, Holtz A, Thunberg R, Olsson P, et al. Purification and characterization of the major oak pollen allergen Que a 1 for component-resolved diagnostics using ImmunoCAP®. International Archives of Allergy and Immunology 2008; 146:203-11.

11. Shevchenko A, Wilm M, Vorm. O, Mann M. Mass spectrometric sequencing of proteins from silver-stained polyacrylamide gels. Analytical Chemistry 1996; 68:850-8.
12. Frohman M A. Rapid amplification of complementary DNA ends for generation of full-length complementary DNAs: thermal RACE. Methods in Enzymology 1993; 218:340-56.
13. Marknell DeWitt Å, Niederberger V, Lehtonen P, Spitzauer S, Sperr W R, Valent P, et al. Molecular and immunological characterization of a novel timothy grass (*Phleum pratense*) pollen allergen, Phl p 11. Clinical and Experimental Allergy 2002; 32:1329-40.
14. Lindblad-Toh K, Wade C M, Mikkelsen T S, Karlsson E K, Jaffe D B, Kamal M, et al. Genome sequence, comparative analysis and haplotype structure of the domestic dog. Nature 2005; 438:803-19.
15. Allen G. Sequencing of proteins and peptides. 1 ed. Amsterdam: Elsevier Science Publishers B.V.; 1981.
16. Spinelli S, Ramoni R, Grolli S, Bonicel J, Cambillau C, Tegoni M. The structure of the monomeric porcine odorant binding protein sheds light on the domain swapping mechanism. Biochemistry 1998; 37:7913-8.
17. Tegoni M, Pelosi P, Vincent F, Spinelli S, Campanacci V, Grolli S, et al. Mammalian odorant binding proteins. Biochim Biophys Acta 2000; 1482:229-40.
18. Mäntyjarvi. Complementary DNA cloning of the predominant allergen of bovine dander: a new member in the lipocalin family. Journal of Allergy and Clinical Immunology 1996; 97:1297-303.
19. Rouvinen J, Rautiainen J, Virtanen T, Zeiler T, Kauppinen J, Taivainen A, et al. Probing the molecular basis of allergy. three-dimensional structure of the bovine lipocalin allergen Bos d 2. Journal of Biological Chemistry 1999; 274:2337-43.
20. Virtanen T, Zeiler T, Rautiainen J, Taivainen A, Pentikainen J, Rytkonen M, et al. Immune reactivity of cow-asthmatic dairy farmers to the major allergen of cow (BDA20) and to other cow-derived proteins. The use of purified BDA20 increases the performance of diagnostic tests in respiratory cow allergy. Clin Exp Allergy 1996; 26:188-96.
21. Ylönen J, Mäntyjärvi R, Taivainen A, Virtanen T. Comparison of the antigenic and allergenic properties of three types of bovine epithelial material. International Archives of Allergy and Immunology 1992; 99:112-7.
22. Ylönen J, Mäntyjärvi R, Taivainen A, Virtanen T. IgG and IgE antibody responses to cow dander and urine in farmers with cow-induced asthma. Clinical and Experimental Allergy 1992; 22:83-90.
23. Rautiainen J, Pentikainen J, Rytkonen M, Linnala-Kankkunen A, Pelkonen J, Virtanen T, et al. Molecular analysis of allergenic proteins in bovine dander. Allergy 1996; 51:378-82.
24. Valenta R, Lidholm J, Niederberger V, Hayek B, Kraft D, Gronlund H. The recombinant allergen-based concept of component-resolved diagnostics and immunotherapy (CRD and CRIT). Clinical & Experimental Allergy 1999; 29:896-904,
25. Åkerstrom B, Flower D R, Salier J P. Lipocalins: unity in diversity. Biochim Biophys Acta. 2000; 1482(1-2):1-8.
26. Flower D R, North A C, Sansom C E. The lipocalin protein family: structural and sequence overview. Biochim Biophys Acta. 2000; 1482(1-2):9-24.
27. Gutiérrez G, Ganfornina M D, Sánchez D. Evolution of the lipocalin family as inferred from a protein sequence phylogeny. Biochim Biophys Acta. 2000; 1482(1-2):35-45.
28. Tegoni M, Pelosi P, Vincent F, Spinelli S, Campanacci V, Grolli S, Ramoni R, Cambillau C. Mammalian odorant binding proteins. Biochim Biophys Acta. 2000; 1482(1-2):229-40.
29 Mäntyjärvi R, Rautiainen J, Virtanen T. Lipocalins as allergens. Biochim Biophys Acta. 2000; 1482(1-2):308-17.

The invention claimed is:

1. A method for producing an allergen composition, comprising adding Bos d 23k allergen of SEQ ID NO: 4, or the mature protein thereof comprising amino acids 19-172 of SEQ ID NO: 4, or a fragment of the Bos d 23k allergen or the mature protein sharing epitopes for antibodies with the Bos d 23k allergen or the mature protein, to a composition comprising an allergen extract and/or at least one other purified allergen component.

2. The method of claim 1, wherein the mature protein or the fragment thereof is added to a composition comprising an allergen extract and/or at least one other purified allergen component.

3. A method for in vitro diagnosis of type I allergy, comprising
   contacting a body fluid sample from a patient suspected of having type I allergy with an allergen immobilized on a solid support, wherein the allergen is Bos d 23k allergen of SEQ ID NO: 4, or the mature protein thereof comprising amino acids 19-172 of SEQ ID NO: 4, or a fragment of the Bos d 23k allergen or the mature protein sharing epitopes for antibodies with the Bos d 23k allergen or the mature protein; and
   detecting the presence, in the sample, of IgE antibodies specifically binding to said allergen,
wherein the presence of such IgE antibodies specifically binding to said allergen, is indicative of a type I allergy.

4. The method of claim 3, wherein the allergen is the mature protein or the fragment thereof.

5. The method of claim 3, wherein the allergen is immobilized on an immunoassay device.

6. The method of claim 3, wherein the allergen is immobilized on a microarray device.

7. The method of claim 3, wherein the allergen is immobilized on a lateral flow assay device.

8. A diagnostic kit for performing a method for in vitro diagnosis of type I allergy, comprising an allergen immobilized on a solid support, wherein the allergen is Bos d 23k allergen of SEQ ID NO: 4, or the mature protein thereof comprising amino acids 19-172 of SEQ ID NO: 4, or a fragment of the Bos d 23k allergen or the mature protein sharing epitopes for antibodies with the Bos d 23k allergen or the mature protein.

9. The kit of claim 8, wherein the allergen is the mature protein or the fragment thereof.

10. The kit of claim 8, wherein the allergen is immobilized on an immunoassay device.

11. The kit of claim 8, wherein the allergen is immobilized on a microarray device.

12. The kit of claim 8, wherein the allergen is immobilized on a lateral flow assay device.

13. The kit of claim 8, including at least one additional purified allergen component.

14. A method for treatment of a Type I allergy to a mammal, comprising administering, to an individual in need of such treatment, a composition comprising Bos d 23k allergen of SEQ ID NO: 4, or the mature protein thereof comprising amino acids 19-172 of SEQ ID NO: 4, or a fragment of the Bos d 23k allergen or the mature protein sharing epitopes for antibodies with the Bos d 23k allergen or the mature protein.

15. The method of claim 14, wherein the composition comprises the mature protein or the fragment thereof.

16. The method according to claim 15, wherein the mammal is bovine.

17. The method according to claim 15, wherein the individual is human.

* * * * *

SEQUENCE LISTING

```
<160> NUMBER OF SEQ ID NOS: 12

<210> SEQ ID NO 1
<211> LENGTH: 525
<212> TYPE: DNA
<213> ORGANISM: Canis familiaris

<400> SEQUENCE: 1
atgaagatcc tactgttgtg tcttgcactc gttttggctt ctgatgccca gctacccctt      60
cctaatgtac tgacacaggt ttcaggacca tggaagacgt tgtacatatc atccaacaac     120
cttgacaaga ttggcgacaa tggaccgttt aggatttata tgagaggtat caatgtggac     180
ataccaagac tcaaaatgtc attcaatttt tacgtcaagg ttgacggaga gtgcgttgaa     240
aactctgttg gggcatcaat aggacgagac aatcttatca agggtgaata taatggtggc     300
aattatttcc gaattattga tatgacccca aatgccctca taggctatga tgtcaatgtg     360
gatagcaaag ggaaaatcac aaaagtggct ttattgatgg gcagaggagc tcatgttaat     420
gaggaggaca ttgcaaagtt caagaagctg agtagagaaa agggtattcc agaagaaaat     480
attatatact taggcgatac tgacaactgt cccaaccatg aataa                     525

<210> SEQ ID NO 2
<211> LENGTH: 174
```

```
<212> TYPE: PRT
<213> ORGANISM: Canis familiaris

<400> SEQUENCE: 2

Met Lys Ile Leu Leu Leu Cys Leu Ala Leu Val Leu Ala Ser Asp Ala
1               5                   10                  15

Gln Leu Pro Leu Pro Asn Val Leu Thr Gln Val Ser Gly Pro Trp Lys
            20                  25                  30

Thr Leu Tyr Ile Ser Ser Asn Asn Leu Asp Lys Ile Gly Asp Asn Gly
        35                  40                  45

Pro Phe Arg Ile Tyr Met Arg Gly Ile Asn Val Asp Ile Pro Arg Leu
    50                  55                  60

Lys Met Ser Phe Asn Phe Tyr Val Lys Val Asp Gly Glu Cys Val Glu
65                  70                  75                  80

Asn Ser Val Gly Ala Ser Ile Gly Arg Asp Asn Leu Ile Lys Gly Glu
                85                  90                  95

Tyr Asn Gly Gly Asn Tyr Phe Arg Ile Ile Asp Met Thr Pro Asn Ala
            100                 105                 110

Leu Ile Gly Tyr Asp Val Asn Val Asp Ser Lys Gly Lys Ile Thr Lys
        115                 120                 125

Val Ala Leu Leu Met Gly Arg Gly Ala His Val Asn Glu Glu Asp Ile
    130                 135                 140

Ala Lys Phe Lys Lys Leu Ser Arg Glu Lys Gly Ile Pro Glu Glu Asn
145                 150                 155                 160

Ile Ile Tyr Leu Gly Asp Thr Asp Asn Cys Pro Asn His Glu
                165                 170

<210> SEQ ID NO 3
<211> LENGTH: 815
<212> TYPE: DNA
<213> ORGANISM: Bos taurus

<400> SEQUENCE: 3
ccttcagctt ctatggaata agggtcttga gagtcaacaa gatggaggtt ttgctgttca     60
gtcttgtcct tggtctgctt tctggcagtc aaggtgaagc tcagggagat gcctcacagt    120
tcacaggaag atggttaacc tattacacgg cagccaataa catagagaag atcactgagg    180
gtgcgccatt ccacgctttc atgcgttacc ttgagtttga tgaagaaaat ggcacaatac    240
tgatgcactt ttatgtcaag gagaatggag aatgcataga aaaatatgcc tcaggcacaa    300
aggaagaaaa ctttatgct gttgactacg cgggtcacaa tgaatttcaa ctcattcggg     360
gggacgcgaa ctctctcttg acgcataatg tcaacgtgga tgaagatggc aaggagacag    420
aactggtgca attatttggc aaaggaaata atgttgaacc ggaatacaaa gaggagtact    480
acaacacagt gagagaaaag gggattccag aagaaatat cctgaacttc atcgataatg     540
ataactgtcc agaggagtga acaaaagtaa ctctgacact tttaaagagt cactgagacc    600
agacatgtcc tcgtctccat ggaatcaaga tcaacaacat gaagatgact ttcctggttt    660
ctgattaaca tgaacctgct ctcttcacac tcgcactccc tttcccatct catctctcct    720
cgtcactaaa tcatgtcccg attggtgtta tttgattgtt gagggttcaa ataaatcaat    780
tgaatatctg ccctgcatac acatgtctgt gcaat                              815

<210> SEQ ID NO 4
<211> LENGTH: 172
<212> TYPE: PRT
<213> ORGANISM: Bos taurus
```

<400> SEQUENCE: 4

Met Glu Val Leu Leu Phe Ser Leu Val Leu Gly Leu Leu Ser Gly Ser
1               5                   10                  15

Gln Gly Glu Ala Gln Gly Asp Ala Ser Gln Phe Thr Gly Arg Trp Leu
            20                  25                  30

Thr Tyr Tyr Thr Ala Ala Asn Asn Ile Glu Lys Ile Thr Glu Gly Ala
        35                  40                  45

Pro Phe His Ala Phe Met Arg Tyr Leu Glu Phe Asp Glu Glu Asn Gly
    50                  55                  60

Thr Ile Leu Met His Phe Tyr Val Lys Glu Asn Gly Glu Cys Ile Glu
65                  70                  75                  80

Lys Tyr Ala Ser Gly Thr Lys Glu Glu Asn Phe Tyr Ala Val Asp Tyr
                85                  90                  95

Ala Gly His Asn Glu Phe Gln Leu Ile Arg Gly Asp Ala Asn Ser Leu
            100                 105                 110

Leu Thr His Asn Val Asn Val Asp Glu Asp Gly Lys Glu Thr Glu Leu
        115                 120                 125

Val Gln Leu Phe Gly Lys Gly Asn Asn Val Glu Pro Glu Tyr Lys Glu
    130                 135                 140

Glu Tyr Tyr Asn Thr Val Arg Glu Lys Gly Ile Pro Glu Glu Asn Ile
145                 150                 155                 160

Leu Asn Phe Ile Asp Asn Asp Asn Cys Pro Glu Glu
                165                 170

<210> SEQ ID NO 5
<211> LENGTH: 22
<212> TYPE: DNA
<213> ORGANISM: Canis familiaris

<400> SEQUENCE: 5
atgaagatcc tactgttgtg tc                                        22

<210> SEQ ID NO 6
<211> LENGTH: 19
<212> TYPE: DNA
<213> ORGANISM: Canis familiaris

<400> SEQUENCE: 6
cagctacccc ttcctaatg                                            19

<210> SEQ ID NO 7
<211> LENGTH: 30
<212> TYPE: DNA
<213> ORGANISM: Canis familiaris

<400> SEQUENCE: 7
gtcagcatat gcagctaccc cttcctaatg                                30

<210> SEQ ID NO 8
<211> LENGTH: 32
<212> TYPE: DNA
<213> ORGANISM: Canis familiaris

<400> SEQUENCE: 8
actgactcga gttcatggtt gggacagttg tc                             32

<210> SEQ ID NO 9
<211> LENGTH: 8

```
<212> TYPE: PRT
<213> ORGANISM: Canis familiaris

<400> SEQUENCE: 9

Ile Ala Glu Asn Gly Pro Phe Arg
1               5

<210> SEQ ID NO 10
<211> LENGTH: 10
<212> TYPE: PRT
<213> ORGANISM: Canis familiaris

<400> SEQUENCE: 10

Gly Glu Tyr Asn Gly Gly Asn Tyr Phe Arg
1               5                   10

<210> SEQ ID NO 11
<211> LENGTH: 11
<212> TYPE: PRT
<213> ORGANISM: Canis familiaris

<400> SEQUENCE: 11

Gly Ala His Val Asn Glu Glu Asp Ile Ala Lys
1               5                   10

<210> SEQ ID NO 12
<211> LENGTH: 15
<212> TYPE: PRT
<213> ORGANISM: Canis familiaris

<400> SEQUENCE: 12

Gly Ile Pro Glu Glu Asn Ile Ile Tyr Leu Gly Asp Thr Asp Asn
1               5                   10                  15
```